United States Patent
Iqbal et al.

(10) Patent No.: US 7,304,186 B2
(45) Date of Patent: Dec. 4, 2007

(54) SYNTHETIC METHOD AND NOVEL CHEMICAL COMPOUNDS

(75) Inventors: Mazhar Iqbal, Liverpool (GB); Paul Evans, Liverpool (GB); Stanley Michael Roberts, Kersbrook (GB)

(73) Assignee: Charterhouse Therapeutics Ltd. (GB)

( * ) Notice: Subject to any disclaimer, the term of this patent is extended or adjusted under 35 U.S.C. 154(b) by 284 days.

(21) Appl. No.: 10/956,532

(22) Filed: Sep. 24, 2004

(65) Prior Publication Data

US 2005/0107477 A1    May 19, 2005

(30) Foreign Application Priority Data

Mar. 25, 2002 (GB) .......................... GB 0207028.2
Mar. 25, 2003 (GB) .................... PCT/GB03/01281

(51) Int. Cl.
*C07C 45/61* (2006.01)
*A61K 31/12* (2006.01)

(52) U.S. Cl. ..................... 568/397; 514/690
(58) Field of Classification Search ............... None See application file for complete search history.

(56) References Cited

OTHER PUBLICATIONS

Suzuki et al. Journal of the American Chemical Society. 1997, vol. 119 (10) p. 2376-2385.*
Shih et al. Journal of Organic Chemistry. 1980, vol. 45 (22), p. 4462-4471.*
Tanikawa et al. Journal of Biological Chemistry. 1998, vol. 273 (29), p. 18522-18527.*
Satoh et al. Journal of Neurochemistry. 2000, vol. 75 (3), p. 1092-1102.*
Satoh et al. Neurotrophic actions of novel compounds designed from cyclopentenone prostaglandins. Journal of Neuroscience, 2001, vol. 77 (1), pp. 50-62.*
Fukushima et al. Antitumor activity, optimum administration method and pharmacokinetics of 13,14-dihydro-15-deoxy-delta7-prostaglandin A1 methyl ester (TEI-9826) integrated in lipid microspheres (Lipo TEI-9826). Anti-Cancer Drugs, 2001, vol. 12 (3), pp. 221-234.*
Suzuki et al., 1997, "$\Delta^7$-Prostaglandin $C_1$: A Primary Metabolite of Antitumor $\Delta^7$-Prostaglandin $A_1$ in the Sera," *Tetrahedron* 53(50): 17009-17014.

* cited by examiner

*Primary Examiner*—Sikarl A. Witherspoon
(74) *Attorney, Agent, or Firm*—Jones Day

(57) ABSTRACT

A method of preparing prostanoid cross-conjugated dienones, via a tandem conjugate addition-Peterson olefination reaction route is described. Such compounds may be useful in medicine and other fields.

34 Claims, 1 Drawing Sheet

SYNTHETIC METHOD AND NOVEL CHEMICAL COMPOUNDS

This application is entitled to and claims priority benefit to International Application No. PCT/GB03/01281, filed Mar. 25, 2003, and Great Britain Application No. 0207028.2, filed Mar. 25, 2002, the entire contents of each of which is incorporated herein by reference.

DESCRIPTION

The present invention relates to a method for preparing certain prostaglandin derivatives for use in medicine and other fields. In particular, the present invention relates to a method for preparing prostanoid cross-conjugated dienones via a tandem conjugate addition-Peterson olefination reaction route.

Prostaglandins (PGs) were discovered almost seventy years ago,[1] but it was not until the 1960s that the area became the focus of attention for many chemists, biochemists and pharmacologists.[2] During the early years of prostaglandin research, various metabolites were identified and synthesized, including PGs containing a cyclopentenone ring system. Thus, PG-As (1) and PG-Bs (2) were formed on treatment of the corresponding PG-E with acid and base, respectively. Similarly, PG-D$_2$ (3) is dehydrated to PG-J$_2$ (4) in vivo and in vitro,[3] and this compound, in turn, isomerizes to □$^{12}$-PG-J$_2$ (5) before further dehydration furnishes Δ$_{12,14}$-15-deoxy-PG-J$_2$ (6) (Scheme 1). The biological activities of PG-As and PG-J$_2$ received relatively scant attention initially but, in recent years, profoundly interesting properties have been revealed.

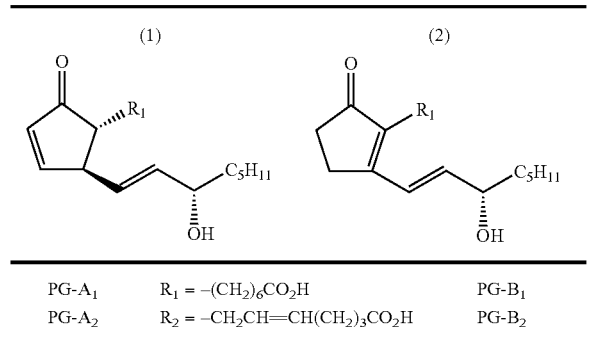

| | | |
|---|---|---|
| PG-A$_1$ | R$_1$ = –(CH$_2$)$_6$CO$_2$H | PG-B$_1$ |
| PG-A$_2$ | R$_2$ = –CH$_2$CH=CH(CH$_2$)$_3$CO$_2$H | PG-B$_2$ |

PG-As were known to be involved in the control of renal function, hormone regulation, vaso- and bronchodilatation.[4] Moreover, evidence for anti-tumour activity of PG-As, PG-Js and the tetra-ene (6) began to accumulate.[5] One important characteristic of the anti-cancer activity of both enone (6) and the closely related compound Δ$^7$-PG-A (7)[6] is that they have little cross-resistance with cis-platin and adriamycin in vivo.[7] The anti-tumour activity has been attributed, at least in part, to the potentiation of turnout necrosis factor-α[8] the inhibition of topoisomerase II[9] and, most recently, to the potent induction of the cytoprotective enzyme glutathione-5-transferase.[10]

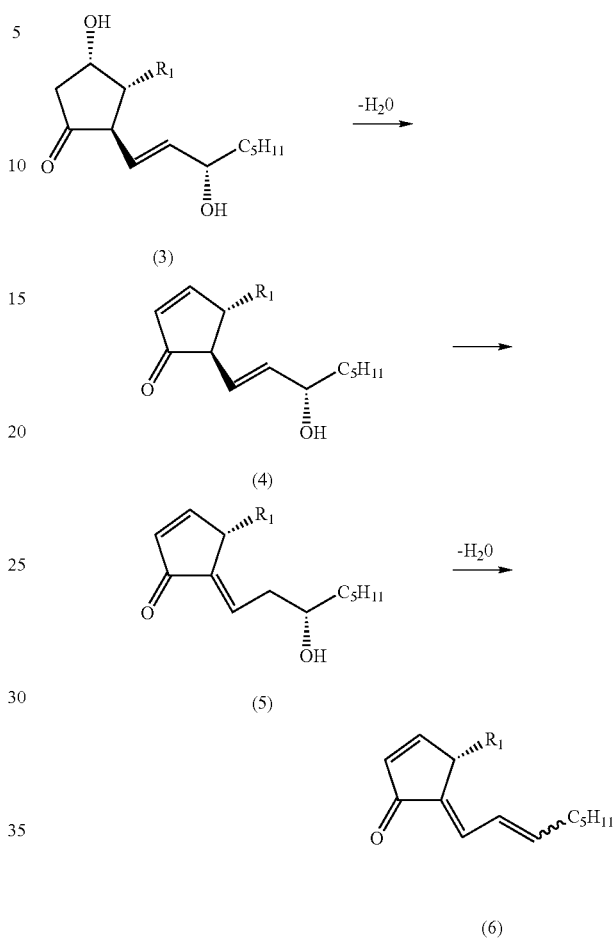

Scheme 1

$R_1$=—$CH_2CH$=$CH(CH_2)_3CO_2H$

In another important discovery, it was found that the cyclopentenone prostaglandins inhibited viral replication by induction of heat-shock protein synthesis via activation of heat shock factors (HSF),[11] and inhibition of nuclear factor (F) kappa B-dependent transcription.[12] A range of viruses including influenza virus,[13] poliovirus[14] and human immunodeficiency virus (HIV)[15] were inhibited due to the cytoprotective effect of the PG-As and PG-Js.[16] In vivo activity was demonstrated in an influenza screen.[17] Both the activation of HSF and the down-regulation of NF-kappa B are associated with binding of the cyclopentenone PGs with the thiol groups of key proteins.[18] In related studies, Noyori and co-workers have studied Michael-type addition of thiols to PG-A$_1$ (1) and Δ$^7$-PG-A$_1$ (7) in vitro, in an endeavour to explain the difference in the anti-tumour and the anti-viral activity between these two compounds.[19] Interestingly PG-A$_2$ (1), PG-J$_2$ (4) and Δ$^{12}$-PG-J$_2$ (5) are known to conjugate, stereoselectively, to glutathione[20] and this may be an important event for the transport, inactivation and/or elimination of the cyclopentenone PGs in vivo. Indeed, it has been mooted that the interaction of PG-As and PG-J$_2$ with glutathione may underlie the well-documented anti-tumour activities of these PGs.[21]

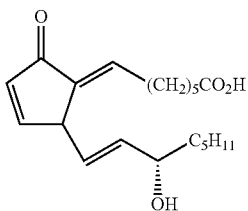

(7)

Another important activity associated with PG-$J_2$ (4) and the prostanoid (6) was reported by two research groups in 1995.[22] It was demonstrated that PG-$J_2$ and its derivatives were efficacious activators of peroxisome proliferator-associated receptors-alpha and -gamma (PPAR-α, PPAR-γ), inter alia, generating the hypothesis that compounds in this group could act as adipogenic agents, in turn giving rise to the hope that novel anti-diabetics could be designed. Some data has suggested that the transcription factor PPAR-γ and, thus, the associated PGs may be involved in the regulation of inflammatory processes,[23] leading to the possibility that PGJ-analogues may be useful in controlling atherosclerosis and rheumatoid arthritis.[24]

Rheumatoid arthritis is a disease associated with massive synovial proliferation, inflammation and angiogenesis. $\Delta^{12,14}$-15-deoxy-PG-$J_2$ suppresses chronic inflammation of adjuvant-induced arthritis in rats. Part of the activity of the prostaglandin (6) may be PPAR-γindependent,[25] acting through inhibition of COX-2 and hence providing a negative feedback control on the production of the pro-inflammatory PG-Es.[26] That the anti-inflammatory activity of the cyclopentenone PGs is due to control of the production of pro-inflammatory primary prostaglandins by indirect action on COX-2 receives backing from other experimental evidence.[27]

The possibility that cyclopentenone prostanoids could be good candidates for a novel class of anti-inflammatory drugs has been strongly enhanced by the recent discovery of the ability of these molecules to inhibit the IkB kinase, IKK. The cyclopentenone PG-$A_1$, and $\Delta^{12,14}$-15-deoxy-PG-$J_2$ have been shown to be direct inhibitors of IKK, by binding to cysteine 179 in the activation loop of the β-subunit of the enzyme.[18] IKK is the key enzyme in triggering the activation of the pro-inflammatory transcription factor NF-kappa-B, by catalysing phosphorylation and consequent degradation sia the proteasome of the NF-kappa-B inhibitory protein InBα. NF-kappa-B is a critical regulator of inflammation and the immune-response, controlling the expression of a variety of pro-inflammatory and chemotactic cytokines, cytokine receptors and enzymes involved in the production of inflammatory mediators. NF-kappa-B also controls the expression of selected viral genes,[28] so that inhibitors of IKK and NF-kappa-B are considered to have interesting potential as novel anti-inflammatory[29] and antiviral drugs.

In addition, PPAR-γ ligands such as the didehydro-PG-$D_2$ (6) are potent inhibitors of angiogenesis in vitro and in vivo and this indicates that PPAR-γ may be an important molecular target for small molecule inhibitors of angiogenesis.[30] Other studies have focussed on PG-mediated apoptosis. For example, it was found that compound (6) inhibited the growth of human pancreatic cancer cells[31] and the growth of lung cancer cell lines through the induction of apoptosis.[32] In some instances, prostanoids of the J-series have unique efficacy as apoptotic agents and it has been shown that these PGs have been shown to be efficacious inhibitors of ubiquitin isopeptidase, an enzyme within the proteasome pathway. Disruption of this pathway by proteasome inhibitors can cause apoptosis. This recent work identifies isopeptidases as novel targets for the development of anti-neoplastic agents.[33] Neuronal apoptosis associated with PPAR-γ activation may contribute to the onset of certain neurodegenerative disorders including Alzheimer's disease. Non-apoptotic (autophagic) cell-death associated with S-phase arrest was observed with PG-treated prostate cancer cells.[34] Enhanced PPAR-γ levels have been found in thyroid carcinoma cell lines and colonic tumours.[35] PG-$J_2$ (4) and $\Delta^{12,14}$-15-deoxy-PG-$J_2$ (6) induce proliferation of cyclooxygenase depleted colorectal cancer cells.[36] Once again, control of the transcription factor may provide a novel target for chemoprevention of colorectal cancer.

Given the volume of biological research in the area of the cyclopentenone prostaglandins, it is surprising that only a few new synthetic approaches to these PGs and analogues have appeared in the chemical literature. $\Delta^7$-PG-$A_1$ methyl ester has been prepared from the enone (8) by adaptation of Noyori's elegant three-component coupling protocol that was invented to gain more efficient access to the primary prostaglandins.[37] Thus, a Michael reaction using an organometallic reagent followed by the trapping of the resultant enolate with methyl 6-formyl hexanoate provided the key intermediate (9), which was readily dehydrated and deprotected to provide the trienone precursor (10), which was in turn readily dehydrated to form the methyl ester of $\Delta^7$-PG-A, (7) (Scheme 2).[38]

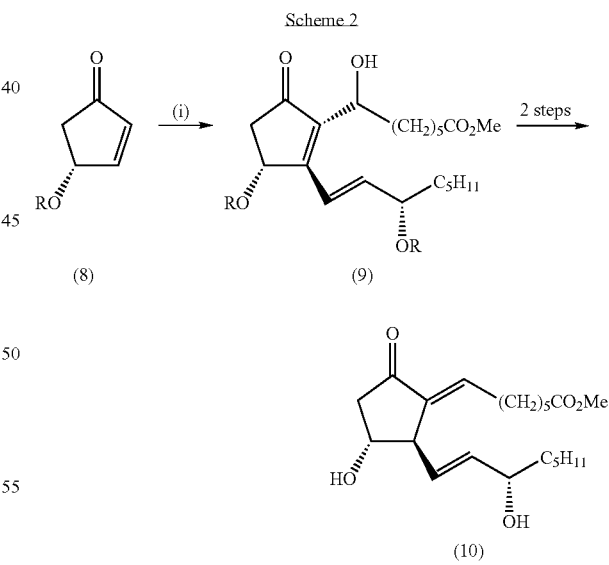

Key reagents and conditions (i) (1E,3S)-LiCH=CHCH(OR)$C_5H_{11}$, ZnMe$_2$, THF −78° C. then HCO(CH$_2$)$_5$CO$_2$Me; R=SiMe$_2$$^t$Bu Similarly, Noyoti's three-component coupling protocol was used to prepare 13, 14 dihydro-15-deoxy-$\Delta^7$-PG-$A_1$ methyl ester,[39] whose enantiomers (11, 12) are about to enter clinical trials as anti-cancer agents.[40]

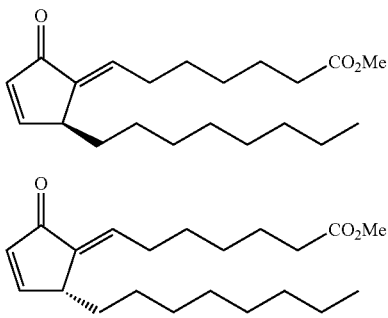

(11)
(12)

Figure 1:
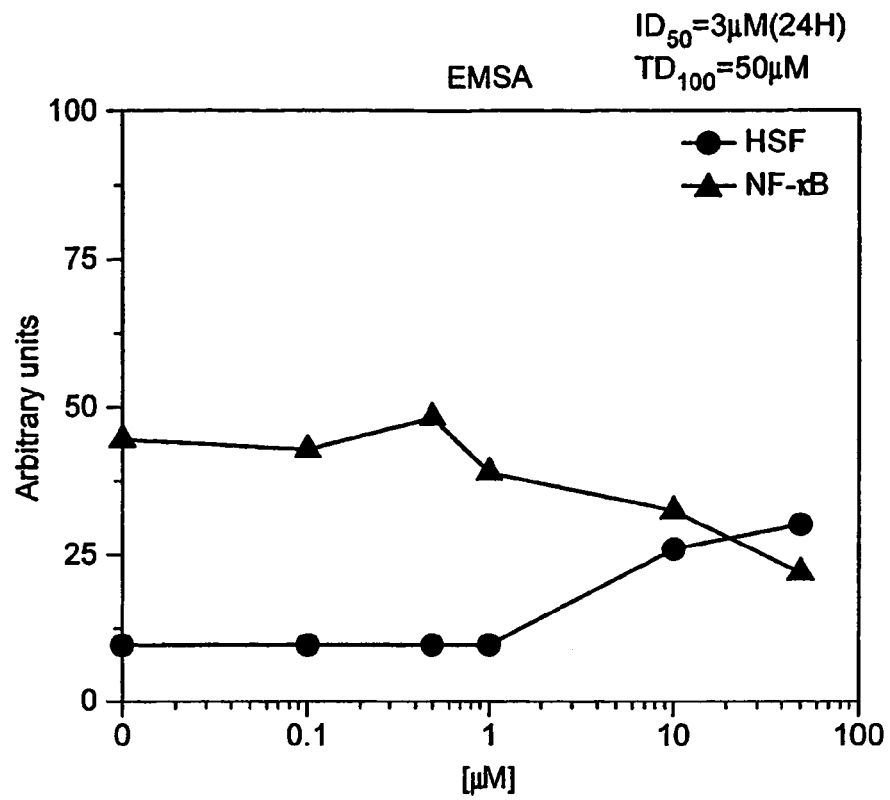
FIG. 1 shows the results of a test, described in Example 6, of the effect of (-)-$\Delta^{12,14}$-15-deoxy-PG-$J_2$ on the reactivity of transcription factors.

It is an object of the present invention to provide an alternative synthetic route to such cross-conjugated dienones and to other cyclic ketones having a 2-alkylidene substituent.

Accordingly, in a first aspect of the invention, there is provided a method for preparing a compound of the formula (I)

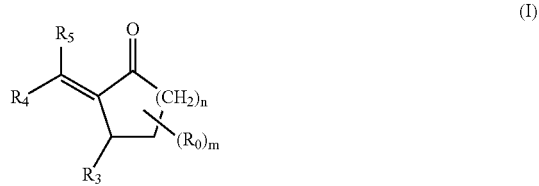

(I)

wherein $R_o$ is hydrogen or any other substituent;

$R_3$, $R_4$ and $R_5$ are each, independently, hydrogen or a substituted or unsubstituted alkyl, alkenyl, alkynyl cycloalkyl, cycloalkenyl, cycloalkynyl aryl or aralkyl group, optionally including at least one heteroatom in its carbon skeleton, or $R_3$ and $R_4$ together form part of a single or a fused ring structure, optionally including at least one heteroatom in its carbon skeleton;

n=0 to 100; and m=0 to (n+1), which comprises reacting a compound of the formula (II)

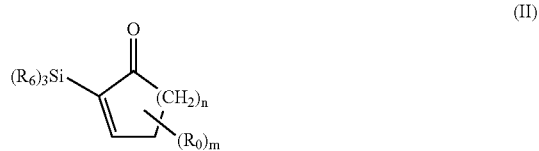

(II)

wherein R is a substituted or unsubstituted alkyl, alkenyl, alkynyl, cycloalkyl, cycloalkenyl, cycloalkynyl, aryl or aralkyl group, optionally including at least one heteroatom in its carbon skeleton, each $R_6$ group being the same or different, with an organometallic compound of the formula (III)

$$R_3M \tag{III}$$

wherein M is a metal ion of an organometallic complex, and reacting the conjugate addition product so obtained in situ with a compound of the formula (IV)

$$R_4COR_5 \tag{IV}$$

to form a compound of the formula (I).

Thus, the method according to the present invention involves the use of a tandem conjugate addition-Peterson olefination sequence on a cyclic enone having a 2-silanyl substituent. Whilst the use of tandem Michael/conjugate addition-Peterson olefination sequences for forming carbon-carbon single and double bonds starting from methyl 2-(trrethylsilyl)propenoate,[41, 42] methyl(1-trimethylsilyl)vinylketone,[43, 44] and α-trimethylsilylbutenolides[45] has previously been described, it is believed to be the first time that such a sequence has been successfully applied to a cyclic ketone, in order to produce a cross-conjugated product.

In compounds of the formula (I), n may be any integer from 0 to 100, preferably from 1 to 30, preferably from 1 to 25, preferably from 1 to 20, preferably from 1 to 15, preferably from 1 to 12, preferably from 1 to 10, and most preferably from 1 to 8. In a particularly preferred embodiment, n=1, 2, 3 or 4, such that the enone moiety forms part of a 5, 6, 7 or 8-membered ring system, especially a 5, 6 or 8-membered ring system. At the same time, m may be any integer from 0 to (n+1), preferably from 1 to n. Where n=1, 2, 3, 4, 5, 6, 7 or 8, m is preferably 1 or 2, especially 2, or another even number.

Where m>0, $R_o$ may be hydrogen or any other substituent, such as, for example, hydroxyl, cyano or a halogen group, or a substituted or unsubstituted alkyl, alkenyl, alkynyl, cycloalkyl, cycloalkenyl, cycloalkynyl, aryl or aralkyl group, optionally including at least one heteroatom in its carbon skeleton. Where m=2, 4, 6, 8 or another even number, at least one $R_0$ group is preferably hydrogen and at least one $R_0$ group on an immediately adjacent carbon atom is preferably hydroxyl or a halogen group, such that the ring system may undergo dehydration or dehydrohalogenation, to form a double bond. Alternatively, at least two $R_0$ groups on two adjacent carbon atoms may together form a structure that will undergo elimination under certain conditions, such as, for example, part of a [4+2]cycloaddition product of a dienophile that is capable of participating in a Retro-Diels-Alder reaction.

$R_3$, $R_4$ and $R_5$ may be hydrogen or any substituted or unsubstituted alkyl, alkenyl, alkynyl, cycloalkyl, cycloalkenyl, cycloalkynyl, aryl or aralkyl group, optionally including at least one heteroatom in its carbon skeleton, or $R_3$ and $R_4$ together may form part of a ring structure, optionally including at least one heteroatom in its carbon skeleton. Preferably, $R_3$ is an alkyl, alkenyl, aryl or aralkyl group, especially a lower alkyl or alkenyl group. In a preferred embodiment, $R_3$ is an alkyl, alkenyl, aryl or aralkyl group, especially a lower alkyl or alkenyl group, including at least one heteroatom in its carbon skeleton. In the latter embodiment, the heteroatom is preferably sulphur and $R_3$ is most preferably a thiolate group. Preferably, $R_4$ is a substituted or unsubstituted alkyl, alkenyl, aryl or aralkyl group, especially a substituted alkyl or alkenyl group. Preferably, $R_5$ is hydrogen, or an alkyl or alkenyl group containing from 1 to 10, especially 1 to 3, carbon atoms. In an especially preferred embodiment, $R_5$ is hydrogen, such that the compound of the formula (IV) used to prepare the compound of the formula (I) is an aldehyde. In a preferred embodiment, $R_5$ is hydrogen and $R_4$ is an aromatic or heteroaromatic group, so that the compound of the formula (IV) is an aromatic or heteroraromatic aldehyde, such as benzaldehyde, furfurylaldehyde, pyridinecarboxaldehyde, pyrrolecarboxaldehyde, quinolinecarboxaldehyde or indolecarboxaldehyde. In embodiments where $R_3$ and $R_4$ together form part of a ring structure, optionally including at least one heteroatom in its carbon skeleton, $R_3$ and $R_4$ are preferably part of a substituted alkyl or alkenyl group containing from 1 to 10 carbon atoms, and especially 2, 3 or 4 carbon atoms. In a preferred embodiment, $R_3$ and $R_4$ together form a —$CH_2CH_2$—, —CH=CH—, —$CH_2CH_2CH_2$—, —$CH_2CH=CH$—, —$CH_2CH_2CH_2CH_2$—, —$CH_2CH_2CH_2S$— or —CH=CH—CH=CH— group.

$R_6$ may be any substituted or unsubstituted alkyl, alkenyl, alkynyl, cycloalkyl, cycloalkenyl, cycloalkynyl, aryl or aralkyl group, optionally including at least one heteroatom in its carbon skeleton, each $R_6$ being the same or different. In a preferred embodiment, at least one $R_6$ group is an aryl or aralkyl group, such as a phenyl or benzyl group, or an alkyl group having from 1 to 8, preferably from 1 to 4, carbon atoms, such as a methyl or t-butyl group. In another embodiment, at least one $R_6$ group is an alkoxy group having from 1 to 8, preferably from 1 to 4, carbon atoms, such as an ethoxy group. Preferably, at least two $R_6$ groups are the same. In a preferred embodiment, all three $R_6$ groups are the same. In an especially preferred embodiment, the $(R_6)_3Si$— group is a trialkylsilyl group in which all three alkyl groups are the same, such as a trimethylsilyl group. In an equally preferred embodiment, the $(R_6)_3Si$— group is a trialkylsilyl group in which at least two of the three alkyl groups are the same, such as a t-butyldimethylsilyl group. In another embodiment, all three $R_6$ groups are different from one another and from the cyclic enone forming the fourth substituent, such that the silicon atom forms a chiral centre. In a further embodiment, at least one $R_6$ group is an asymmetric chiral pool based substituent. In a preferred embodiment, $R_6$ is α-pinene, whose enantiomers are commercially available in homochiral form. In these embodiments, the use of an asymmetric substituent in the compound of the formula II may undergo partial or total enantioselective conjugate addition and Peterson olefination, leading to some or complete enantioenrichment of the compound of formula I. In an especially preferred embodiment, at least one $R_6$ group forms a linker group, such that the compound of the formula II is linked to a solid phase, such as Wang's resin or Merrifield's resin. This last embodiment enables the initial reaction steps to be carried out by way of a solid phase synthesis, thereby facilitating recovery and purification. In such embodiments, at least one of the two remaining $R_6$ groups may be hydrogen.

M may be any metal ion or metal atom capable of forming an organometallic complex or an organometallic compound. In the context of the present invention, an "organometallic" compound will be defined as one in which there is a bonding interaction (ionic or covalent, localized or delocalized) between one or more carbon atoms of an organic group or molecule and a main group, transition, lanthanide, or actinide metal atom (or atoms). In addition, organic derivatives of the metalloids (boron, silicon, germanium, arsenic, and tellurium) are included in this definition. In a preferred embodiment, M is a main group metal or metalloid, such as lithium, beryllium, magnesium, aluminium, gallium, germanium or tin, especially lithium or magnesium. In an equally preferred embodiment, however, M may be a transition metal of the first, second or third transition series, especially the first or second transition series, or may be an actinide or a lanthanide. In this latter embodiment, M is preferably copper, zinc or cadmium.

In an especially preferred embodiment, the invention provides a method for preparing a compound of the formula (V)

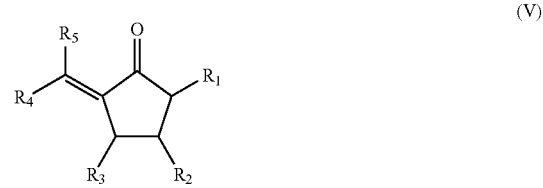

wherein $R_1$ and $R_2$ are each, independently, hydrogen, hydroxyl, cyano or a halogen group, or a substituted or unsubstituted alkyl, alkenyl alkynyl, cycloalkyl, cycloalkenyl, cycoalkynyl, aryl, or aralkyl group, optionally including at least one heteroatom in its carbon skeleton, or $R_1$ and $R_2$ together form part of a single or a fused ring structure, optionally including at least one heteroatom in its carbon skeleton, which comprises reacting a compound of the formula (VI)

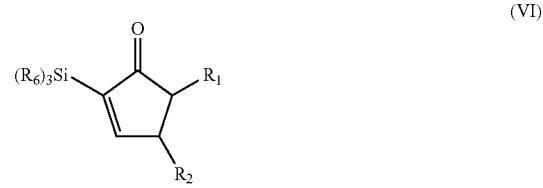

with an organometallic compound of the formula (III)

$R_3M$ (III)

and reacting the conjugate addition product so obtained in situ with a compound of the formula (IV)

$R_4COR_5$ (IV)

to form a compound of the formula (V).

Thus, in this embodiment, the invention provides an alternative synthetic route to compound (10) above, which route does not require a dehydration step in order to form the cross-conjugated enone group. $R_1$, $R_2$, $R_3$, $R_4$, $R_5$, $R_6$ and M are each as previously defined above. In an embodiment, $R_1$ is hydrogen or a substituted or unsubstituted alkyl, alkenyl or alkynyl group having from 1 to 12 carbon atoms and optionally including at least one heteroatom in its carbon skeleton. $R_1$ is preferably hydrogen. $R_2$ is preferably hydrogen, hydroxyl, cyano or a halogen group, or is a substituted or unsubstituted alkyl alkenyl or alkynyl group, having from 1 to 12 carbon atoms and optionally including at least one heteroatom in its carbon skeleton. Preferably, $R_2$ is hydroxyl. In an especially preferred embodiment, $R_2$ is hydroxyl or a halogen group and $R_1$ is hydrogen. In another embodiment, $R_1$ and $R_2$ are joined, such that the compound of the formula (V) has a bicyclic, tricyclic or polycyclic structure. In this last embodiment, $R_1$ and $R_2$ may form part of a [4+2]-cycloaddition product of a dienophile. Each of $R_3$ and $R_4$ is preferably a substituted or unsubstituted alkyl alkenyl or alkynyl group having from 1 to 12 carbon atoms, 1 to 11, 1 to 10, 1 to 9, 1 to 8, 1 to 7, 1 to 6, 1 to 5, 1 to 4, 1 to 3 or 1 to 2 carbon atoms, optionally including at least one heteroatom in its carbon skeleton. In a preferred embodiment, each of $R_3$ and $R_4$ has from 6 to 8 carbon atoms and also includes at least one heteroatom in its carbon skeleton, especially one or more oxygen atoms in the form of a hydroxyl or a carboxylate group. Preferably, at least one of $R_3$ and $R_4$ includes a double bond within its structure. Preferably, $R_4$ is —$(CH_2)_5COOH$, —$(CH_2)_5COOR$, —$CH=CH(CH_2)_3COOH$, —$CH=CH(CH_2)_3COOR$, —$CH=CH-CH=CH-CH_2-COOH$ or —$CH=CH-CH=CH-CH_2-COOR$, where R is an alkyl group of from 1 to 3 carbon atoms, especially a methyl group. Preferably, $R_3$ is —$(CH_2)_7CH_3$, —$CH=CH-CH(OH)-C_5H_{11}$, or —$CH=CH-CH(OH)CH(CH_4)C_4H_9$. $R_5$ is preferably hydrogen or an alkyl group having from 1 to 4 carbon atoms, especially from 1 to 3 carbon atoms. Preferably, $R_5$ is hydrogen, such that the compound of the formula (IV) is an aldehyde. In an especially preferred embodiment, $R_1$ is hydrogen, $R_2$ is hydroxyl, $R_3$ is —$CH=CH-CH(OH)-C_5H_{11}$, $R_4$ is —$(CH_2)_5COOMe$ and $R_5$ is hydrogen, such that the compound of the formula (V) is a triene precursor of the formula (10), which can be readily dehydrated to form the methyl ester of $\Delta^7$-$PG$-$A_1$ (7) described above. $R_6$ is preferably a phenyl or benzyl group, or a lower alkyl group having from 1 to 4 carbon atoms, such as a methyl or t-butyl group. In an alternative embodiment, at least one $R_6$ group is a chiral auxiliary, such as α-pinene, or forms a linker group that serves to attach the silyl group to a solid phase, such as Merrifield's resin. M is preferably a lithium or magnesium ion or atom, such that the compound of the formula (III) is an organolithium or an organomagnesium compound.

Preferably, the compound of the formula (VI) is reacted with the compound of the formula (III) so that the conjugate addition reaction occurs diastereoselectively. In order to achieve this, the conditions of the reaction may be selected such that they provide thermodynamic or kinetic control, or the substituents on the compound of the formula (III) or the compound of the formula (VI) may be chosen such that the reaction is controlled by steric factors. The use of chiral auxiliaries as substituents on the silanyl group of the compound of the formula (VI) may also be of some assistance in this regard. In another embodiment, the compound of the formula (VI) does not contain any chiral auxiliaries as substituents, but is chiral per se and is capable of transferring its chirality to the compound of the formula (V). Preferably, the compound of the formula (VI) is enantiomerically pure, so that the compound of the formula (V) may be obtained in enantiomerically pure form. The compound of the formula (VI) preferably reacts with the compound of the formula (III) to form a conjugate addition product or enolate of the formula (VII)

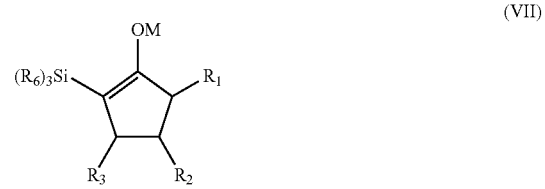

The resulting enolate (VII) may either be allowed to form the corresponding 2-silanyl cyclic ketone, or the transient α-silyl carbanion species may be trapped with a carbonyl compound to yield the corresponding β-silylalkoxide, which will undergo instantaneous elimination to form the cross-conjugated olefin. In the latter case, the stereochemistry of the exocyclic double bond may be controlled using "harder" or "softer" counter-ions on the enolate intermediate (VII). Thus, the use of harder counter-ions, such as $Li^+$, favours the formation of trans-exocyclic enones, whereas the use of softer counter-ions, such as $MgX^+$ and $ZnX^+$, favours the formation of cis-exocyclic enones. The metal cationic species result from the conjugate addition of the organometallic compound of the formula (III). If the compound of formula (III) is a lithium cuprate of formula $(R_3)_2CuLi$, for example, the counter-ion is $Li^+$. If the compound of formula (III) is a Grignard reagent of formula $R_3MgX$, for example, the counterion is $MgX^+$. However, such counterions may be exchanged. $ZnCl_2$, for example, may be used to transmetallate a $Li^+$ enolate into a $Zn^{2+}$ enolate.

The compound of the formula (III) may be any organometallic compound that will undergo conjugate addition across the 2-(trisubstituted)silylenone. Preferably, the organometallic compound of the formula (III) is an organolithium, organocopper or organomagnesium complex, or any combination thereof, but other organometallic compounds, such as organozinc or organocadmium compounds, may be equally effective. In an especially preferred embodiment, the organometallic complex is a copper lithium complex of the formula (VIII)

$$R_3R_7CuLi \hspace{2cm} (VIII)$$

wherein $R_3$ and $R_7$ are each, independently, as defined in claim 1 for $R_3$. The use of such compounds in conjugate addition reactions is well documented in the chemical literature.[45] Such compounds are especially preferred for selectively preparing trans-exocyclic enones. In a preferred embodiment, $R_3$ and $R_7$ are each, independently, an alkyl, alkenyl or alkynyl group having from 1 to 12 carbon atoms and optionally including at least one heteroatom in its carbon skeleton. Preferably, $R_3$ and $R_7$ are the same. In an equally preferred embodiment, the organometallic complex is a Grignard reagent of the formula (IX)

$$R_3MgX \hspace{2cm} (IX)$$

wherein $R_3$ is as defined in claim 1 and X is a halogen group selected from fluorine, chlorine, bromine, iodine or astatine, especially bromine or iodine. Such Grignard reagents are preferred for preparing predominantly cis-exocyclic enones.

In this case, the Grignard reagent may be used directly, but will generally be used in the presence of a suitable catalyst, such as copper (I) iodide, in order to promote conjugate rather than ketone addition. However, other catalytic agents suitable for this purpose will be known to those skilled in the art. In the foregoing embodiments, the inventive method preferably comprises the step of reacting a compound of the formula (X)

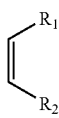

(X)

with a tri-substituted silanylacetylene and $CO_2(CO)_8$ in a Pauson-Khand reaction,[46] to form the compound of the formula (VI). In a preferred embodiment, the tri-substituted silanylacetylene is trimethylsilanylacetylene or t-butyldimethylsilanylacetylene. In an equally preferred embodiment, at least one $R_6$ group is a chiral auxiliary such as α-pinene, such that the compound of the formula X may undergo a stereoselective Pauson-Khand reaction with the tri-substituted silanylacetylene and $CO_2(CO)_8$. In an alternative embodiment, at least one $R_6$ group may form a linker group, such that the tri-substituted silanylacetylene is linked to as solid phase and the Pauson-Khand reaction may be carried out via solid phase synthesis. Using a Pauson-Khand reaction, the compound of the formula (VI) may be synthesized in high yield in a single step. In an especially preferred embodiment, the inventive method is used for preparing a compound of the formula (XI)

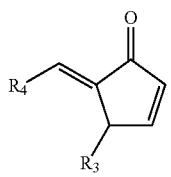

(XI)

wherein $R_4$ and $R_3$ are as defined above, which comprises preparing a compound of the formula (V) by a method as described above and then causing the compound of the formula (V) to undergo simultaneous elimination of $R_1$ and $R_2$, in order to form the compound of the formula (XI). In a preferred embodiment, one of $R_1$ and $R_2$ is hydrogen and the other is hydroxyl and the compound of the formula (V) undergoes dehydration, to form the compound of the formula (XI). In another embodiment, one of $R_1$ and $R_2$ is hydrogen and the other is a halogen group and the compound of the formula (V) undergoes dehydrohalogenation, in order to form the compound of the formula (XI). In an especially preferred embodiment, the compound of the formula (V) is a compound of the formula (XII)

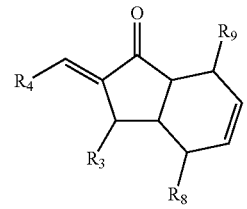

(XII)

wherein $R_8$ and $R_9$ are each, independently, hydrogen or a substituted or unsubstituted alkyl, alkenyl, alkynyl, cycloalkyl, cycloalkenyl, cycloalkynyl, aryl, or aralkyl group, optionally including at least one heteroatom in its carbon skeleton, or $R_8$ and $R_9$ together form part of a single or fused ring structure, optionally including at least one heteroatom in its carbon skeleton, and wherein the compound of the formula (XII) undergoes a Retro-Diels-Alder reaction to form the compound of the formula (XI). Preferably, $R_8$ and $R_9$ together form a transannular ethylene group, such that the Retro-Diels-Alder reaction produces 1,3-cyclohexadiene in addition to the compound of the formula (I). In an equally preferred embodiment, $R_8$ and $R_9$ together form a methylene group, such that the Retro Diels-Alder reaction produces 1,3-cyclopentadiene in addition to the compound of the formula (XI).

In a second aspect of the invention, there is provided a method for preparing a compound of the formula (XIII)

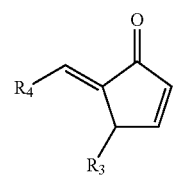

(XIII)

wherein $R_3$ and $R_4$ are each, independently, hydrogen or a substituted or unsubstituted alkyl, alkenyl, alkynyl cycloalkyl, cycloalkenyl, cycloalkynyl aryl or aralkyl group, optionally including at least one heteroatom in its carbon skeleton, or $R_3$ and $R_4$ together form part of a single or a fused ring structure, optionally including at least one heteroatom in its carbon skeleton;

which comprises reacting norbornadiene with trimethylsilanylacetylene and $CO_2(CO)_8$ to form a compound of the formula (XIV)

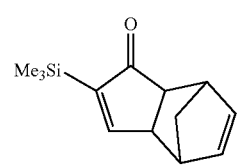

(XIV)

reacting the compound of the formula (XIV) with an organometallic compound of the formula (III)

wherein M is a metal ion of an organometallic complex, and reacting the resultant conjugate addition product in situ with a compound of the formula (XV)

to form a compound of the formula (XVI)

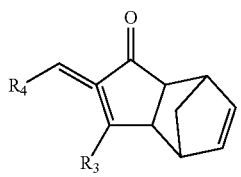

and heating the compound of the formula (XVI) to form the compound of the formula (XIII).

In this aspect, the invention provides a facile synthetic route which can be used to produce a cross-conjugated dienone compound of the formula (XIII) in good yield.

In a preferred embodiment, norbornadiene is reacted with trinethylsilanylacetylene and $CO_2(CO)_8$ by stirring a solution of the components in a suitable solvent at or around ambient temperature for 1 to 72 hours, preferably 1 to 48 hours, most preferably 1 to 24 hours, to form a compound of the formula (XIV). In another embodiment, norbornadiene is reacted with trimethylsilanylacetylene and $CO_2(CO)_8$ using flash vacuum pyrolysis. In an equally preferred embodiment, norbornadiene is reacted with trimethylsilanylacetylene and $CO_2(CO)_8$ by heating a mixture of these compounds in a suitable solvent in a microwave for 1 to 120 minutes, preferably from 1 to 60 minutes, preferably from 1 to 30 minutes and most preferably from 1 to 10 minutes. The compound of the formula (XIV) may exist in the exo- or endo-configuration, depending upon whether the 5-membered cyclopentenone ring is on the same side ("exo") or the opposite side ("endo") as the methylene bridge of the [2.2.1]-bicycloheptene ring. The reaction of norbornadiene with trimethylsilanylacetylene and $CO_2(CO)_8$ by stirring a solution of the components in a solvent at ambient temperature generally produces exo-form selectively, typically in a ratio of exo: endo of about 9:1. However, the reaction conditions may be controlled to favour formation of the endo-form if so desired. In addition, each of the exo- and endo-forms of the compound of formula (XIV) may exist in the form of enantiomers. In a preferred embodiment, the conditions for the reaction between norbornadiene, trimethylsilanylacetylene and $CO_2(CO)_8$ are chosen such that the reaction occurs substantially asymmetrically. Suitable conditions for the preparation of the exo-form of the compound of the formula (XIV) in its two enantiomerically pure forms have been described in the literature.47 Since the compound of the formula (XV) attacks the compound of the formula (XIV) from its least sterically-hindered face, the use of a single enantiomer of the compound of the formula (XIV) results in the formation of a single enantiomer of the compound of the formula (XIII). Thus, the use of a single enantiomer of the exo- or endo-form of the compound of the formula (XIV) allows stereochemical information to be relayed to the compound of the formula (III). $R_3$, $R_4$ and M are each as previously defined above in relation to the invention in its first aspect. Each of $R_3$ and $R_4$ is preferably a substituted or unsubstituted alkyl, alkenyl or alkynyl group having from 1 to 12 carbon atoms, 1 to 11, 1 to 10, 1 to 9, 1 to 8, 1 to 7, 1 to 6, 1 to 5, 1 to 4, 1 to 3 or 1 to 2 carbon atoms, optionally including at least one heteroatom in its carbon skeleton. In a preferred embodiment, each of $R_3$ and $R_4$ has from 6 to 8 carbon atoms and also includes at least one heteroatom in its carbon skeleton, especially one or more oxygen atoms in the form of a hydroxyl or a carboxylate group. Preferably, at least one of $R_3$ and $R_4$ includes a double bond within its structure. Preferably, $R_4$ is —$(CH_2)_5COOH$, —$(CH_2)_5COOR$, —$CH=CH(CH_2)_3COOH$, —$CH=CH(CH_2)_3COOR$, —$CH=CH—CH=CH—CH_2—COOH$ or —$CH=CH—CH=CH—CH_2—COOR$, where R is an alkyl group of from 1 to 3 carbon atoms, especially a methyl group. Preferably, $R_3$ is —$(CH_2)_7CH_3$, —$CH=CH—CH(OH)—C_5H_{11}$, or —$CH=CH—CH(OH)CH(CH_3)C_4H_9$. In an embodiment, $R_3$ is —$CH_2—CH=CH(CH_2)_3COOH$ and $R_4$ is —$CH_2CH(OH)C_5H_{11}$, such that the compound of the formula (XIII) is $\Delta^{12}$-PG-$J_2$ (5) above. In another embodiment, $R_3$ is —$CH_2—CH=CH(CH_2)_3COOH$ and $R_4$ is —$CH=CH—C_5H_{11}$, such that the compound of the formula (XIII) is $\Delta^{12,14}$-15-deoxy PG-$J_2$ (6) as described above. In an especially preferred embodiment, $R_3$ is —$C_8H_{17}$ and $R_4$ is —$(CH_2)_5COOMe$, such that the compound of the formula (XIII) is either compound (11) above, compound (12) above or a racemic mixture thereof. The compound of the formula (XV) may be heated in the presence of a Lewis acid and, optionally, a dienophile, to form the compound of the formula (XIII). The use of a Lewis acid enables the reaction to be carried out at low temperatures, preferably between ambient temperature and about 50° C., whilst the optional inclusion of a dienophile provides a means of trapping the reverse-coupled diene that is formed by the Retro-Diels-Alder reaction. Preferably, the compound of the formula (XV) is heated in the presence of $Me_2AlCl$ or $MeAlCl_2$ or the like, and in the presence of maleic anhydride, to form the compound of the formula (XIII).

In a third aspect of the invention, there is provided a compound of the formulae (I), (V), (XI) or (XIII) obtained or obtainable by a method according to the invention in its first or second aspects. Preferably, the compound of the formula (I) has one of the following structures:

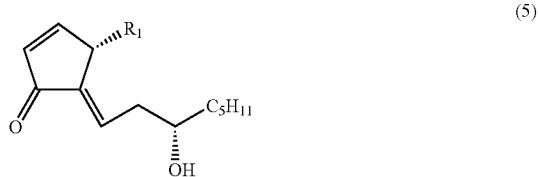

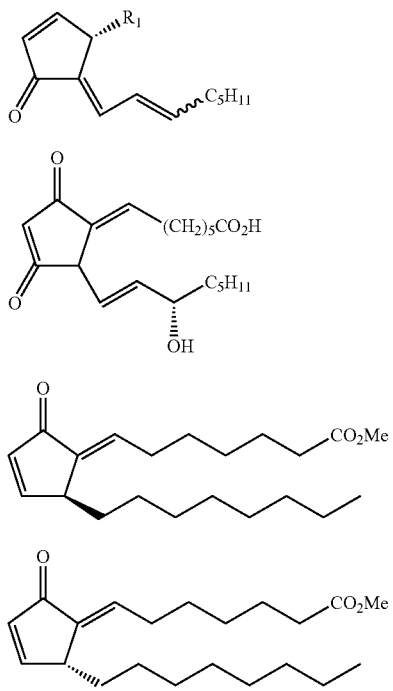

wherein $R_1$=—$CH_2CH=CH(CH_2)_3CO_2H$.

In a preferred embodiment, the compound of the formula (I) has the following structure:

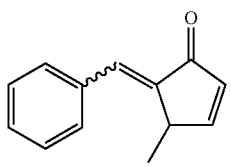

In an especially preferred embodiment, the compound of the formula (I) has the following structure:

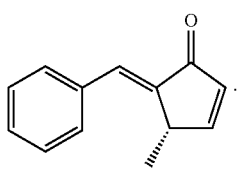

In a fourth aspect of the invention, there is provided a compound according to the invention in its third aspect, for use in therapy. In one embodiment, the compound is for use as anti-viral agent. In another embodiment, the compound is for use in treating cancer, especially a cancer is selected from the group consisting of pancreatic cancer, prostate cancer, colorectal cancer and thyroid cancer. In a further embodiment, the compound is for use as an anti-inflammatory agent. In an alternative embodiment, the compound is for use in inhibiting angiogenesis. In a yet further embodiment, the compound is for use in treating atherosclerosis and/or for treating rheumatoid arthritis. In another embodiment, the compound is for use as an apoptotic agent. In an especially preferred embodiment of the invention, the compound has the following structure

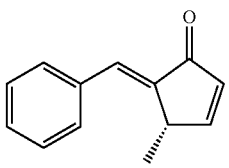

and is for use in treating viral infections.

In a fifth aspect of the invention, there is provided a pharmaceutical composition comprising a compound according to the invention in its third or fourth aspects and a pharmaceutically acceptable excipient. Suitable pharmaceutically acceptable excipients for inclusion in the inventive compositions are well-known to those skilled in the art and include, without limitation, preserving agents, solubilising agents, stabilising agents, wetting agents, emulsifiers, sweeteners, colourants, odourants, salts (the compounds of the present invention may themselves be provided in the form of a pharmaceutically acceptable salt), buffers, coating agents or antioxidants. A pharmaceutical composition within the scope of the present invention may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) routes. Such a composition may be prepared by any method known in the art of pharmacy, for example by admixing one or more active ingredients with a suitable carrier.

In a sixth aspect of the invention, there is provided a method of treating a patient in need of therapy, comprising administering a therapeutically effective amount of a compound according to the invention in its third or fourth aspects to said patient.

In a seventh aspect of the invention, there is provided a method of treating a patient in need of anti-viral therapy, comprising administering a therapeutically effective amount of a compound according to the invention in its third or fourth aspects to said patient.

In an eighth aspect of the invention, there is provided a method of treating a patient in need of cancer therapy, comprising administering a therapeutically effective amount of a compound according to the invention in its third or fourth aspects to said patient.

In a ninth aspect of the invention, there is provided a method of treating a patient in need of anti-inflammatory therapy, comprising administering a therapeutically effective amount of a compound according to the invention in its third or fourth aspects to said patient.

In a tenth aspect of the invention, there is provided a method of treating a patient in need of anti-viral therapy, comprising administering a therapeutically effective amount of a compound having the following structure to said patient:

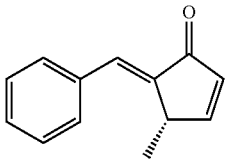

In order that the invention may be more fully understood, it will now be described, by way of illustration only, with reference to the following specific examples.

EXAMPLE 1

The synthesis of 4-methyl-5-[1-phenyl-meth-(E)-ylidene]-cyclopent-2-enone (6), which can also be named as 4-methyl-5E-benzylidenecyclopent-2-enone and has been assigned the reference number CTC-150, by the method according to the present invention is illustrated in Scheme 3 below.

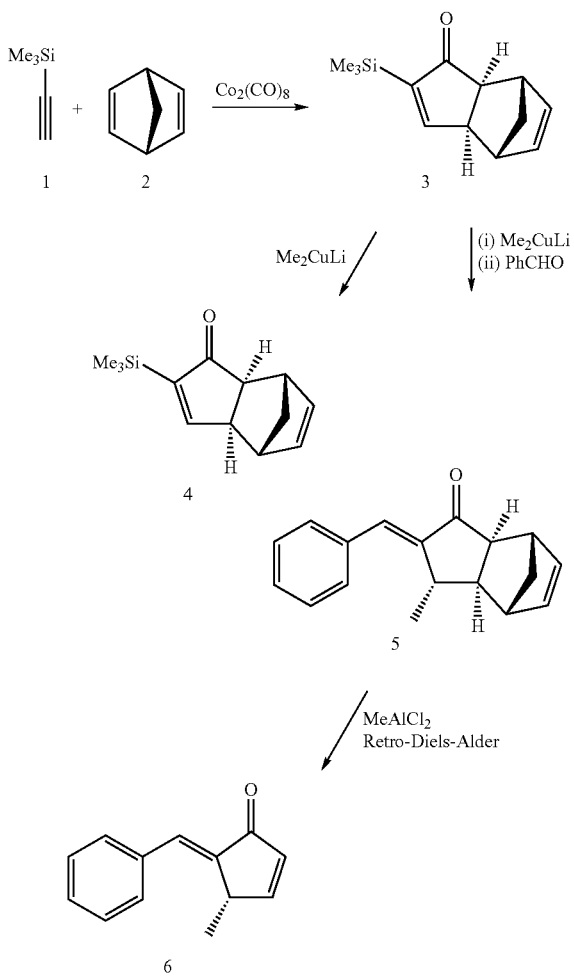

Preparation of exo-2-trimethylsilanyl-3a,4,7,7a-tetrahydro-4,7-methano-inden-1-one (3) by Pauson-Khand Reaction Under nitrogen at room temperature, a solution of trimethylsilanylacetylene (1.44 cm$^3$, 10.19 mmol., 1 eq.) in dichloromethane (40 cm$^3$) was treated with $CO_2(CO)_8$ (3.50 g, 10.24 mmol., 1 eq.). Stirring was continued for 24 hours. TLC analysis (hexane) indicated formation of the corresponding cobalt complex. Norbornadiene (1.2 cm$^3$, 11.12 mmol., 1.1 eq.) was added, the reaction was cooled to 0° C. and 4-methylmorpholine N-oxide (11.93 g, 101.84 mmol., 10 eq.) was added in five portions. Stirring was continued for 3 days, before silica (ca. 25 g) was added and the solvent was removed under reduced pressure. Purification by flash column chromatography (Hex-Et$_2$O; 19:1) afforded initially exo-2-trimethylsilanyl-3a,4,7,7a-tetrahydro-4,7-methano-inden-1-one (3) (1.20 g, 54%) followed by endo-trimethylsilanyl-3a,4,7,7a-tetrahydro-4,7-methano-inden-1-one (0.130 g, 6%) [exo-(3):endo-(3); 9:1]. $R_f$=0.25 (Hex-Et$_2$O; 19:1) [endo-(3); $R_f$=0.15 (Hex-Et$_2$O; 19:1)]; $\delta_H$ (400 MHz, CDCL$_3$) −0.17 (9H, s, CH$_3$), 1.05 (1H, d, J 11.25 Hz, CH$_2$), 1.22 (1H, d, J 11.25 Hz, CH$_2$), 2.01 (1H, d, J 6.25 Hz, CH), 2.52 (1H, s, CH), 2.72-2.74 (1H, m, CH), 2.80 (1H, s, CH), 6.11-6.18 (1H, m, CH), 6.21-6.30 (1H, m, CH), 7.65 (1H, d, J 2.5 Hz, CH); $\delta_C$ (100 MHz, CDCL$_3$) −2.1, 41.1, 42.8, 43.7, 51.9, 53.2, 137.2, 138.1, 152.0, 172.7, 213.0; m/z (CI) 219 (MH$^+$, 100%); Found C, 71.50; H, 8.31%, $C_{13}H_{18}SiO$ requires C, 71.60; H, 8.30%.

Preparation of 3-methyl-2-[1-phenyl-meth-(E)-ylidene]-2,3,3a,4,7,7a-hexahydro-4,7-methano-inden-1-one (5) by Tandem Conjugate-Addition Peterson Olefination Reaction At −78° C. under nitrogen, a slurry of CuI (636 mg, 3.34 mmol., 1.5 eq.) in Et$_2$O (25 cm$^3$) was treated dropwise with a 1.6 M solution of MeLi in hexane (4.2 cm$^3$, 6.72 mmol., 3.0 eq.). The reaction was warmed to −10° C. over a period of 2 hours. This solution was cooled to −20° C., before a cooled (−20° C.) solution of enone (3) (485 mg, 2.23 mmol., 1 eq.) in Et$_2$O (25 cm$^3$) was added dropwise. The flask containing the enone (3) was washed, Et$_2$O (5 cm$^3$) was added and this was transferred to the reaction mixture. Stirring was continued for 1.5 hours during which time the temperature rose to 10° C. Upon cooling to −78° C., benzaldehyde (0.35 cm$^3$, 3.44 mmol., 1.5 eq.) was added. The reaction was stirred for 3 hours and warmed from −78° C. to 10° C. NH$_4$Cl (25 cm$^3$) was added and the resultant aqueous phase was further extracted with Et$_2$O (3×25 cm$^3$). The combined organic extracts were dried over MgSO$_4$, filtered and the solvent removed in vacuo. The crude product was purified by flash column chromatography (Hex-Et$_2$O; 19:1) affording 3-methyl-2-[1-phenyl-meth-(E)-ylidene]-2,3,3a,4,7,7a-hexahydro-4,7-methano-inden-1-one (5) as a colourless solid (520 g, 93%). Recrystallization from hexane gave crystals of (5) suitable for X-ray crystallography. $R_f$=0.15 (Hex-Et$_2$O; 19:1); $\delta_H$ (400 MHz, CDCl$_3$) 1.25 (3H, d, J 7.0 Hz, CH$_3$), 1.28 (1H, dt, J 1.5, 9.5 Hz, CH$_2$), 1.36 (1H, d, J 9.5 Hz, CH$_2$), 1.93 (1H, d, J 7.5 Hz, CH), 2.48 (1H, d, J 7.5 Hz, CH), 2.86 (1H, s, CH), 3.12 (1H, s, CH), 3.19 (1H, q, J 7.0 Hz, CH), 6.18-6.26 (2H, m, CH), 7.28 (1H, d, J 2.0 Hz, CH), 7.34-7.44 (3H, m, ArH), 7.57 (2H, d, J 7.5 Hz, ArH); $\delta_C$ (100 MHz, CDCl$_3$) 21.2, 38.9, 43.2, 48.5, 49.2, 49.5, 53.3, 128.8, 129.4, 130.7, 133.4, 135.9, 137.6, 139.0, 145.1, 209.0; m/z (EI) 250 (M$^+$ 25%), 183 (100%), 156

(50%), 141 (50%), 128 (40%), 115 (70%), 91 (50%), 66 (90%); Found C, 85.95; H, 7.42%, $C_{18}H_{18}O$ requires C, 86.36; H, 7.25%.

Preparation of 4-methyl-5-[1-phenyl-meth-(E)-ylidene]-cyclopent-2-enone (6) (Compound CTC-150) by Retro-Diels-Alder Reaction Under nitrogen, a solution of 3-methyl-2-[1-phenyl-meth-(E)-ylidene]-2,3,3a,4,7,7a-hexahydro-4,7-methano-inden-1-one (5) (250 mg, 1 mmol., 1 eq.) and maleic anhydride (490 mg, 5 mol., 5 eq.) in dichloromethane (10 cm$^3$) was treated with a 1.0 M solution of $MeAlCl_2$ in hexane (1.1 cm$^3$, 1.1 mmol., 1.1 eq.). This mixture was heated to reflux for 5 hours. Silica (ca. 2.5 g) was added and the solvent was removed under reduced pressure. Flash column chromatography (Hex-EtOAc; 3:1) gave 4-methyl-5-[1-phenyl-meth-(E)-ylidene]-cyclopent-2-enone (6) (compound CTC-150) (138 mg, 75%) as a colourless solid. $R_f$=0.5 (Hex-EtOAc; 3:1); $\delta_H$ (400 MHz, CDCl$_3$) 1.22 (3H, d, J 7.0 Hz, CH$_3$), 3.84-4.00 (1H, m, CH), 6.40 (1H, dd, J 1.75, 5.75 Hz, CH), 7.39-7.44 (4H, ArH), 7.54 (2H, d, J 7.0 Hz, AH, 7.60 (1H, ddd, J 1.0, 2.5, 5.75 Hz, CH); $\delta_C$ (100 MHz, CDCl$_3$) 16.3, 38.8, 128.7, 129.3, 130.6, 131.7, 133.6, 134.8, 138.3, 163.9, 197.4; Found C, 84.66; H, 6.60%, $C_{13}H_{12}O$ requires C, 84.78; H, 6.57%.

EXAMPLE 2

The synthesis of 4-methyl-5-[1-(4-nitrophenyl)-meth-(E)-ylidene]-cyclopent-2-enone (8) by the method according to the present invention is illustrated in Scheme 4 below.

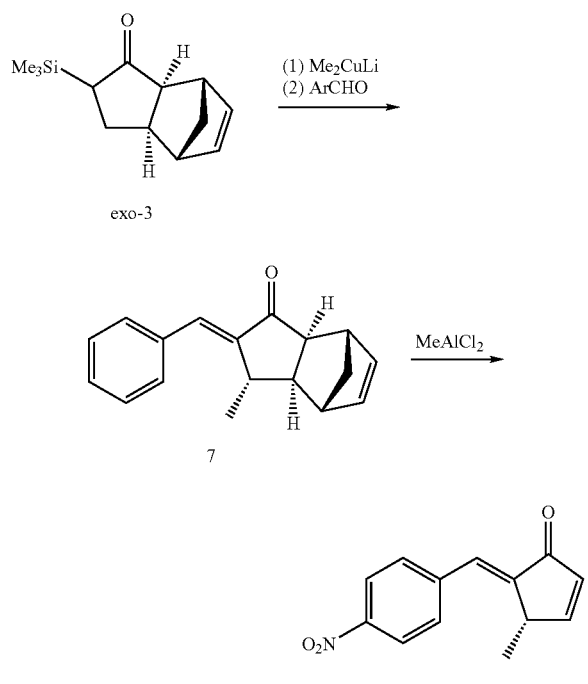

Scheme 4

Preparation of 3-methyl-2-[1-(4-nitrophenyl)-meth-(E)-ylidene]-2,3,3a,4,7,7a-hexahydro-4,7-methano-inden-1-one (7) by Tandem Conjugate-Addition Peterson Olefination Reaction Exo-2-trimethylsilanyl-3a,4,7,7a-tetrahydro-4,7-methano-inden-1-one (3) was prepared as described in Example 1 above. Following the procedure described in Example 1 above, 3 (485 mg, 2.22 mmol, 1 eq.) in Et$_2$O (10 cm$^3$) was treated with a solution of MeCuLi in Et$_2$O (25 cm$^3$) generated from CuI (636 mg, 3.34 mmol, 1.5 eq.) and a 1.6 M solution of MeLi in Et$_2$O (4.2 cm$^3$, 6.72 mmol, 3 eq.). After TLC indicated formation of the conjugate adduct, 4-nitrobenzaldehyde (504 mg, 3.33 mmol 1.5 eq.) in benzene (5 cm$^3$) was added [washed with THF (5 cm$^3$)]. Standard work-up as described above followed by flash column chromatography (Hex-EtOAc; 3:1) afforded adduct (7) (600 mg, 92%) as a yellow crystalline solid. Analytically pure (7) was obtained on recrystallisation from EtOAc. $R_f$=0.35 (Hex-EtOAc; 3:1); $\delta_H$ (400 MHz, CDCl$_3$) 1.24 (3H, d, J 7.0 Hz, CH$_3$), 1.30-1.35 (2H, m, CH$_2$), 2.01 (1H, d, J 7.5 Hz, CH), 2.54 (1H, d, J 7.5 Hz, CH), 2.92 (1H, s(br), CH), 3.14 (1H, s(br), CH), 3.22 (1H, q, J 7.0 Hz, CH), 6.23 (1H, dd, J 2.5, 5.5 Hz, CH), 6.28 (1H, dd, J 3.0, 5.5 Hz, CH), 7.28 (1H, d, J 2.25 Hz, CH), 7.72 (2H, d, J 8.5 Hz, ArH), 8.27 (2H, d, J 8.5 Hz, ArH); $\delta_C$ (100 MHz, CDCl$_3$) 21.1, 38.9, 43.5, 48.6, 49.2, 49.4, 53.3, 123.9, 130.2, 130.9, 137.5, 139.0, 141.3, 147.5, 148.8, 208.6; m/z (CI) 313 (MNH$_4^+$, 80%), 296 (MH$^+$, 35%), 266 (90%), 247 (65%), 230 (MH-$C_5H_6^+$, 100%); Found 296.12835, $C_{18}H_{18}NO_3$ requires 296.12866; Found C, 72.73; H, 5.75; N, 4.52%, $C_{18}H_{17}NO_3$ requires C, 73.21; H, 5.80; N, 4.74%.

Preparation of 4-methyl-5-[1-(4-nitrophenyl)-meth-(E)-ylidene]-cyclopent-2-enone (8) by Retro-Diels-Alder Reaction Following the Retro-Diels-Alder procedure described in Example 1 above, adduct (7) (220 mg, 0.746 mmol, 1 eq.) and maleic anhydride (365 mg, 3.72 mmol, 5 eq.) in dichloromethane (20 cm$^3$) was treated with a 1.0 M solution of MeAlCl$_2$ in hexane (0.75 cm$^3$, 0.75 mmol, 1 eq.) and heated to reflux for 3.5 hours. The reaction was cooled before Et$_2$O (50 cm$^3$) and 0.5 M NaOH (50 cm$^3$) were added. The resultant aqueous layer was extracted with Et$_2$O (2×50 cm$^3$) and the combined organic extracts were dried over MgSO$_4$. Filtration, pre-absorption onto silica (ca. 5 g) and purification by flash column chromatography (Hex-EtOAc; 3:1) afforded the cyclopentenone (8) (145 mg, 85%) as a pale yellow solid. $R_f$=0.30 (Hex-EtOAc; 3:1); $\delta_H$ (400 MHz, CDCl$_3$) 1.20 (3H, d, J 7.5 Hz, CH$_3$), 3.93-4.01 (1H, m, CH), 6.47 (1H, dd, J 1.75, 6.0 Hz, CH), 7.42 (1H, s, CH), 7.66 (1H, dd, J 2.5, 6.0 Hz, CH), 7.68 (2H, d, J 8.5 Hz, ArH), 8.28 (2H, d, J 8.5 Hz, ArH); $\delta_C$ (100 MHz, CDCl$_3$) 16.4, 38.6, 123.9, 128.8, 130.8, 131.2, 133.6, 141.2, 141.6, 164.3, 196.6; m/z (CI) 247 (MNH$_4^+$, 5%), 230 (MH$^+$, 10%), 200 (100%); Found 230.08171, $C_{13}H_{12}NO_3$ requires 230.08164, (−0.3 ppm); Found C, 67.93; H, 4.85; N, 6.10%, $C_{13}H_{11}NO_3$ requires C, 69.09; H, 4.84; N, 6.11%.

EXAMPLE 3

The synthesis of 4-methyl-5-[1-(4-methoxyphenyl)-meth-(E)-ylidene]-cyclopent-2-enone (10) by the method according to the present invention is illustrated in Scheme below.

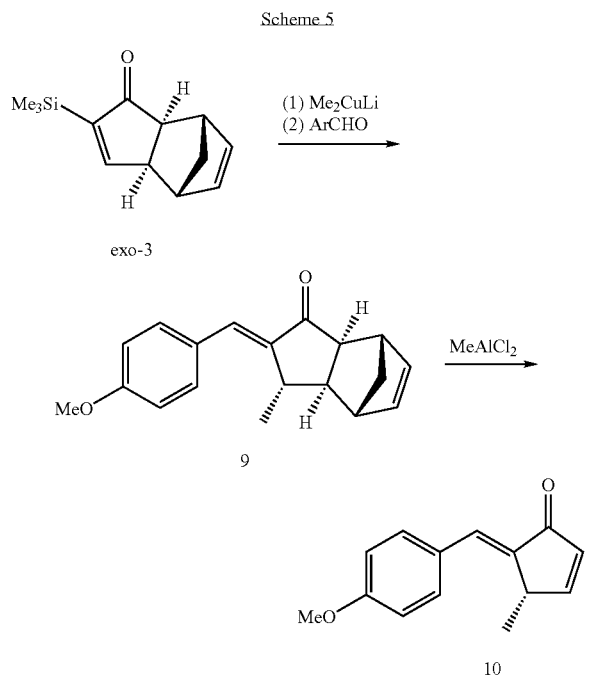

Preparation of 3-methyl-2-[1-(4-methoxyphenyl)-meth-(E)-ylidene]-2,3,3a,4,7,7a-hexahydro-4,7-methano-inden-1-one (9) by Tandem Conjugate-Addition Peterson Olefination Reaction Exo-2-trimethylsilanyl-3a,4,7,7a-tetrahydro-4,7-methano-inden-1-one (3) was prepared as described in Example 1 above. Following the procedure described in Example 1 above, a solution of Me$_2$CuLi in Et$_2$O (25 cm$^3$), prepared from CuI (636 mg, 3.33 mmol 1.5 eq.) and a 1.6 M solution of MeLi in hexane (4.2 cm$^3$, 6.72 mmol, 3.0 eq.), was treated with 3 (485 mg, 2.22 mmol, 1 eq.). On formation of the conjugate adduct, as determined by TLC analysis, p-methoxybenzaldehyde (455 mg, 3.34 mmol, 1.5 eq.) was added. Following standard work-up described above and purification by flash column chromatography (Hex-EtOAc; 3:1) the adduct (9) (281 mg, 45%) was isolated as a colourless solid. R$_f$=0.35 (Hex-EtOAc; 3:1); δ$_H$ (400 MHz, CDCl$_3$) 1.25 (3H, d, J 7.25 Hz, CH$_3$), 1.23-1.28 (1H, m, CH$_2$), 1.94 (1H, d, J 7.5 Hz, CH), 7.48 (1H, d, J 7.5 Hz, CH), 2.85 (1H, s, CH), 3.09-3.18 (2H, m, CH), 3.86 (3H, s, CH$_3$), 6.20 (1H, dd, J 3.0, 5.5 Hz, CH), 6.23 (1H, dd, J 3.0, 5.5 Hz, ArH), 6.95 (2H, d, J 8.5 Hz, ArH), 7.28 (1H, s, CH), 7.54 (2H, d, J 8.5 Hz, ArH); m/z (CI) 281 (MNH$_4^+$, 70%), 215 ME-C$_5$H$_6^+$, 100%); Found 281.15390, C$_{19}$H$_{21}$O$_2$ requires 281.15414, (−0.9 ppm); Found C, 81.60; H, 7.31%, C$_{19}$H$_{20}$O$_2$ requires C, 81.43; H, 7.14%.

Preparation of 4-methyl-5-[1-(4-methoxyphenyl)-meth-(E)-ylidene]-cyclopent-2-enone (10) by Retro-Diels-Alder Reaction Following the Retro-Diels-Alder procedure described in Example 1 above, 9 (350 mg, 1.25 mmol, 1 eq.) and maleic anhydride (613 mg, 6.26 mmol, 5 eq.) in dichloromethane (25 cm$^3$) was treated with a 1.0 M solution of MeAlCl$_2$ in hexane (1.25 cm$^3$, 1.25 mmol, 1 eq.) and heated to reflux for 35 hours. Et$_2$O (50 cm$^3$) and 0.5 M NaOH (50 cm$^3$) were added. The resultant aqueous layer was extracted with Et$_2$O (2×50 cm$^3$) and the combined organic extracts were dried over MgSO$_4$. Filtration, pre-absorption onto silica (ca. 5 g) and purification by flash column chromatography (Hex-EtOAc; 3:1) afforded 10 (182 mg, 68%) as a colourless solid. R$_f$=0.25 (Hex-EtOAc; 3:1); δ$_H$ (400 MHz, CDCl$_3$) 1.21 (3H, d, J 7.5 Hz, CH$_3$), 3.83-3.92 (1H, m, CH), 3.85 (3H, s, CH$_3$), 6.38 (1H, dd, J 2.0, 6.0 Hz, CH), 6.90 (2H, d, J 8.5 Hz, ArH), 7.34 (1H, s, CH), 7.49 (2H, d, J 8.5 Hz, ArH), 7.57 (1H, ddd, J 1.0, 2.5, 6.0 Hz, ArH); δ$_C$ (100 MHz, CDCl$_3$) 16.3, 38.8, 55.3, 114.2, 127.1, 131.4, 133.5, 136.1 160.5, 163.4, 197.5; m/z (CI) 214 (MH$^+$, 100%), 186 (75%), 171 (100%); Found 214.09934, C$_{14}$H$_{14}$O$_2$ requires 214.09937, (−0.1 ppm).

EXAMPLE 4

The synthesis of 4-octyl-5-[1-phenyl-meth-(E)-ylidene]-cyclopent-2-enone (15) by the method according to the present invention is illustrated in Scheme 6 below.

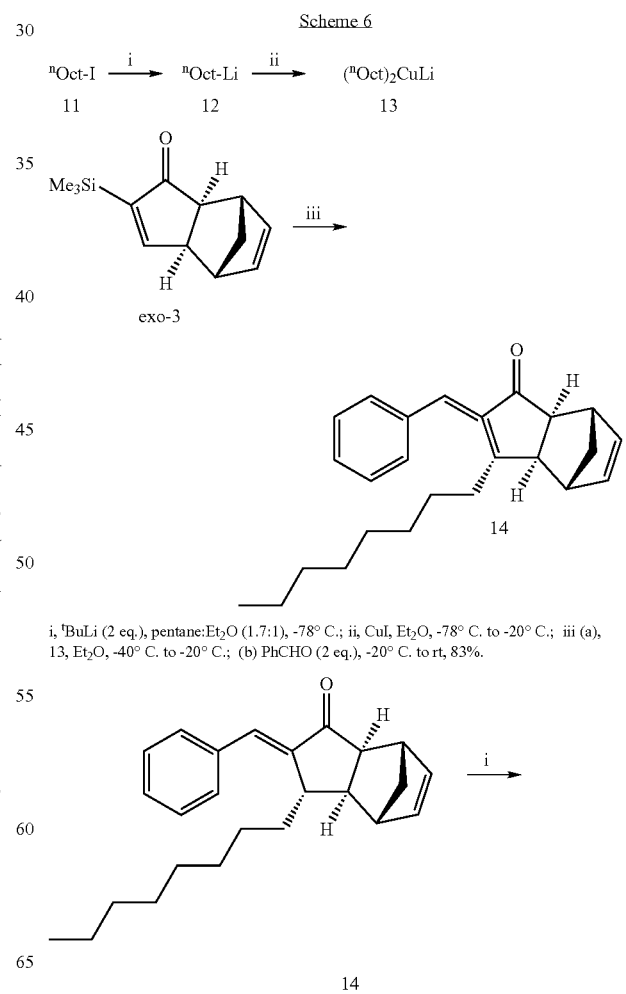

i, $^t$BuLi (2 eq.), pentane:Et$_2$O (1.7:1), -78° C.; ii, CuI, Et$_2$O, -78° C. to -20° C.; iii (a), 13, Et$_2$O, -40° C. to -20° C.; (b) PhCHO (2 eq.), -20° C. to rt, 83%.

-continued

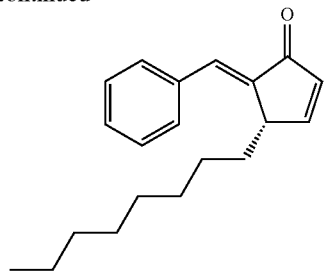

15 i, MeAlCl$_2$, MA (5 eq.), DCM, 40° C., 76%

Preparation of 3-octyl-2-[1-phenyl-meth-(E)-ylidene]-2,3,3a,4,7,7a-hexahydro-4,7-methano-inden-1-one (14) by Tandem Conjugate-Addition Peterson Olefination Reaction Under N$_2$, a 1.7 M solution of tert-butyllithium in pentane (4.9 cm$^3$, 8.33 mmol, 4 eq.) was added dropwise to a solution of octyl iodide (11) (0.75 cm$^3$, 4.15 mmol, 2 eq.) in a mixture of pentane (17 cm$^3$) and Et$_2$O (10 cm$^3$) at −78° C. Stirring was continued at −78° C. for 15 minutes before warning to room temperature over 1 hour. This solution of octyl lithium (12) was cooled to −78° C. and added to a slurry of CuI (395 mg, 2.07 mmol, 1 eq.) in Et$_2$O (10 cm3) at −78° C. via a cannula. The mixture was warmed to −20° C. over 1 hour. The resultant cuprate (13) was cooled to −40° C. and a solution of the enone (3) (452 mg, 2.07 mmol, 1 eq.) in Et$_2$O (5 cm$^3$) was added dropwise [washed with Et$_2$O (2 cm$^3$)]. After stirring for 1 hour, during which time the temperature reached −20° C., TLC analysis indicated loss of (3) and formation of a faster moving spot (Hex-EtOAc; 9:1). Benzaldehyde (0.42 cm$^3$, 4.13 mmol, 1 eq.) was added and the reaction was stirred for 18 hours, during which period room temperature was reached. Saturated NH$_4$Cl (25 cm$^3$) and EtOAc (25 cm$^3$) were added and the resultant aqueous layer was further extracted with EtOAc (2×25 cm$^3$). The combined organic extracts were dried over MgSO$_4$. Filtration followed by solvent removal in vacuo and flash column chromatography (Hex-EtOAc; 19:1) afforded the title compound (14) (604 mg, 84%) as a viscous yellow liquid. R$_f$=0.25 (Hex-EtOAc; 19:1); δ$_H$ (400 MHz, CDCl$_3$) 0.88 (3H, t, J 6.5 Hz, CH$_3$), 1.18-1.52 (15H, m, CH$_2$), 1.64-1.73 (1H, m, CH$_2$), 2.05 (1H, d, J 7.5 Hz, CH), 2.47 (1H, d, J 7.5 Hz, CH), 2.82 (1H, s, CH), 3.01-3.09 (1H, m, CH), 3.12 (1H, s, CH), 6.23 (1H, dd, J 2.75, 5.5 Hz, CH), 6.28 (1H, dd, J 3.0, 5.5 Hz, CH), 7.30 (1H, d, J 2.0 Hz, CH), 7.34-7.44 (3H, m, ArH), 7.56 (2H, d, J 7.0 Hz, ArH); δ$_C$ (100 MHz, CDCl$_3$) 14.1, 22.6, 26.9, 29.2, 29.5, 29.6, 31.8, 34.7, 43.3, 44.4, 46.5, 48.4, 49.8, 53.7, 128.7, 129.4, 130.7, 133.4, 135.0, 137.6, 138.9, 144.3, 209.2; m/z (CI) 349 (MH$^+$, 10%), 283 (MH−C$_5$H$_6^+$, 100%); Found 349.25394, C$_{25}$H$_{33}$O requires 349.25314 (+2.5 ppm); Found C, 85.9; H, 9.4%, C$_{25}$H$_{32}$O requires C, 86.2; H, 9.2%.

Preparation of 4-octyl-5-[1-phenyl-meth-(E)-ylidene]-cyclopent-2-enone (15) by Retro-Diels-Alder Reaction Under N$_2$, a mixture of (14) (541 mg, 1.55 mmol, 1 eq.) and maleic anhydride (762 mg, 7.77 mmol, 5 eq.) in dichloromethane (33 cm$^3$) was treated with a 1.0 M solution of MeAlCl$_2$ (1.95 cm$^3$, 1.95 mmol, 1.25 eq.). The reaction mixture was heated to reflux (ca. 40° C.) for 6 hours. The mixture was cooled and silica (ca. 5 g) was added before the solvent was removed in vacuo. Purification by flash column chromatography (Hex-EtOAc; 9:1) afforded 5 (100 mg, 18%) and the title compound (15) (334 mg, 76%) as a pale yellow liquid. R$_f$=0.25 (Hex-EtOAc; 9:1); ν$_{max}$ (neat/cm$^{-1}$) 3058, 2926, 2855, 1698, 1633, 1583, 1495; δ$_H$ (400 MHz, CDCl$_3$) 0.86 (3H, t, J 6.5 Hz, CH$_3$), 1.13-1.30 (12H, m, CH$_2$), 1.33-1.44 (1H, m, CH$_2$), 1.78-1.89 (1H, m, CH$_2$), 3.90-3.96 (1H, m, CH), 6.44 (1H, dd, J 1.75, 6.0 Hz, CH), 7.35-7.45 (3H, m, ArH), 7.39 (1H, s, CH), 7.52 (2H, d, J 7.5 Hz, ArH), 7.70 (1H, dd, J 2.5, 6.0 Hz, CH); δ$_C$ (100 MHz, CDCl$_3$) 14.0, 22.6, 26.0, 29.1, 29.2, 29.4, 30.1, 31.7, 43.9, 128.6, 129.2, 130.4, 131.6, 134.4, 134.8, 137.2, 162.4, 197.5; m/z (CI) 283 (MH$^+$, 100%); Found 283.20650, C$_{20}$H$_{27}$O requires 283.20618 (+1.2 ppm).

EXAMPLE 5

The synthesis of compound TEI-9826 by the method according to the present invention is illustrated in Scheme 7 below.

Preparation of 1-methoxycycloheptene (2)

At 0° C., cycloheptanone (1) (5 cm$^3$, 42.61 mmol, 1 eq.), trimethylorthoformate (5.2 cm$^3$, 46.88 mmol, 1.1 eq.) and anhydrous toluenesulphonic acid (40 mg, 0.213 mmol, 0.05 eq.) were allowed to warm to room temperature and left to stand for 2 days. Crude $^1$H-NMR spectroscopy indicated formation of the intermediate ketal. Distillation, initially at atmospheric pressure, then at water aspirator pressure (ca. 15 mm/Hg) afforded the product 2 (3.82 g, 71%) as a colourless liquid (b.p. 130-140° C./15 mm/Hg). δ$_H$ (250 MHz, CDCl$_3$) 1.35-1.55 (4H, m, CH), 1.59-1.74 (2H, m, CH$_2$), 1.97-2.08 (2H, m, CH$_2$), 2.12-2.25 (2H, m, CH$_2$), 3.39 (3H, s, CH$_3$), 4.67 (1H, t, J 7.0 Hz, CH); m/z (CI) 127 (MH+, 100%).

Preparation of 7-oxoheptanoic Acid Methyl Ester (3)

A solution of 2 (4.68 g, 0.037 mol, 1 eq.) in dichloromethane (50 cm$^3$) was cooled to −78° C. and treated with a stream of ozone for 4 hours. During this period the temperature rose to −20° C. Dimethylsulfide (15 cm$^3$, 0.204 mol. 5.5 eq.) was added and the reaction was left to stir at room temperature for 48 hours. Under reduced pressure, the dichloromethane and excess dimethylsulfide were removed before purification by flash column chromatography (Hex-EtOAc; 1:1), followed by distillation (b.p. 95-105° C./15 mm/Hg) afforded the aldehyde (3) (1.52 g, 26%) as a colourless liquid. R$_f$=0.1 (streak) (Hex-EtOAc; 1:1); δ$_H$ (400 MHz, CDCl$_3$) 1.33-1.42 (2H, m, CH$_2$), 1.65 (4H, pent, J 7.5 Hz, CH), 2.32 (2H, t, J 7.5 Hz, CH$_2$), 2.45 (2H, dt, J 1.5, 7.5 Hz, CH$_2$), 3.64 (3H, s, CH$_3$), 9.79 (1H, m, CHO); δ$_C$ (100 MHz, CDCl$_3$) 21.6, 24.5, 28.5, 33.7, 43.5, 51.3, 173.8, 202.2; m/z (CI) 176 (MNH$_4^+$, 100%), 159 (MH$^+$, 70%).

Scheme 7

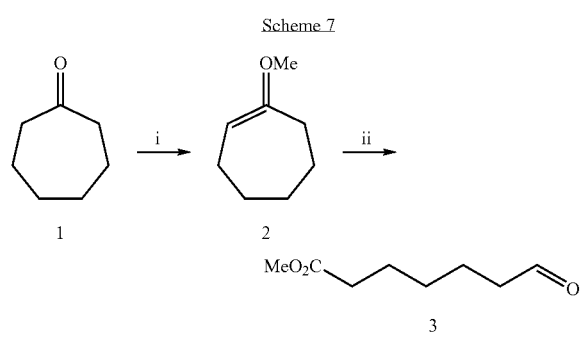

i, (MeO)₃CH, cat. TsOH, rt, 71%; ii, (a) O₃, -78° C. to -40° C.; (b) Me₂S, -78° C. to rt, 26%

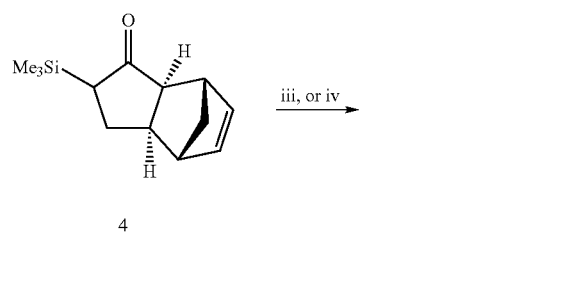

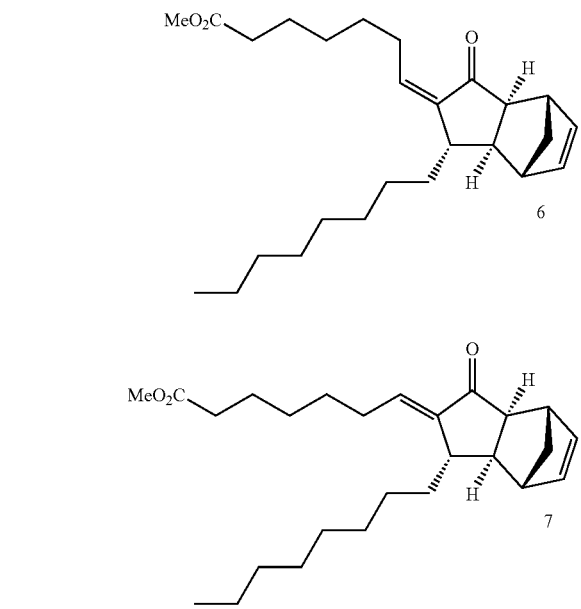

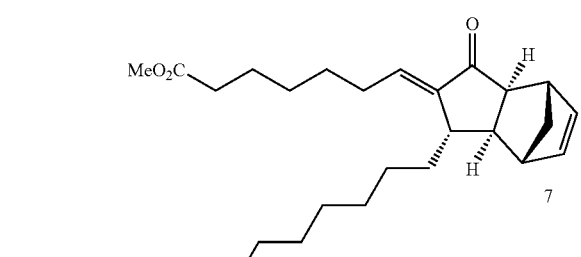

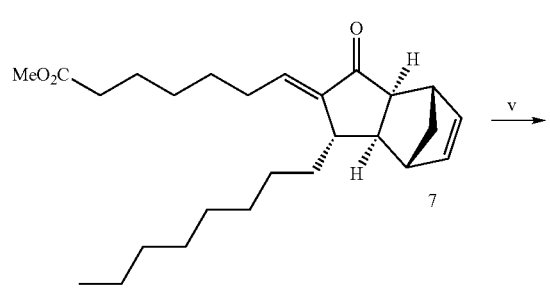

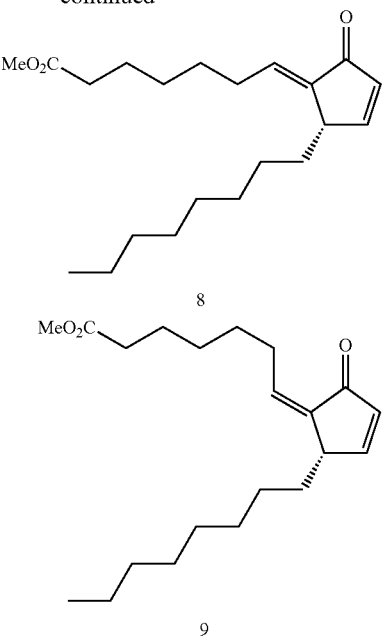

iii, (a) (ⁿOct)₂CuLi, pentane:Et₂O (1:1), -40° C. to -10° C.; (b) 3, -78° C. to -10° C., 81% [7:6; >95:5];
iv, (a) ⁿOctMgBr, CuI (10 mol%), Et₂O, -45° C. to -5° C.; (b) 3, -78° C. to rt, 57%; 6:7; 65:35;
v, MeAlCl₂MA, DCM, 50° C., 69%.

Preparation of (±)-7-[1-octyl-3-oxo-1,3,3a,4,7,7a-hexahydro-4,7-methanoinden-(2E)-ylidene]heptanoic Acid Methyl Ester (7)

Under nitrogen at −78° C., a solution of octyl iodide (0.63 cm³, 3.49 mmol, 2 eq.) in a mixture of pentane (15 cm³) and Et₂O (7.5 cm³) was treated dropwise with a 1.7 M solution ᵗBuLi in pentane (4.1 cm³, 6.97 mmol, 4 eq.). After stirring at −78° C. for 15 minutes, the reaction was warmed to room temperature over 1.5 hours. The cloudy white solution was re-cooled to −78° C. and then added via a cannula to a −78° C. slurry of CuI (333 mg, 1.75 mmol, 1 eq.) in Et₂O (10 cm³). The resultant black/brown octyl cuprate solution was warmed from −78° C. to −20° C. over a period of 1 hour. The cuprate was then cooled to −40° C., before enone (4) (381 mg, 1.75 mmol, 1 eq.) in Et₂O (5 cm³, washed with 2 cm³) was added dropwise. Over 1.25 hours, the temperature rose to −10° C. and TLC analysis (Hex-EtOAc; 19:1) indicated consumption of enone. The resulting enolate was re-cooled to −78° C. and the aldehyde (3) (415 mg, 2.63 mmol, 1.5 eq.) was added dropwise. Stirring was continued for 5 hours. During this time, the temperature rose from −78° C. to −10° C. Saturated NH₄Cl (50 cm³) was added and the resultant mixture was extracted with EtOAc (3×50 cm³). The combined organic extracts were dried over MgSO₄, filtered and the solvent removed under reduced pressure. Purification by flash column chromatography (Hex-EtOAc; 9:1) afforded the title compound (7) (567 mg, 81%) as a colourless liquid. $R_f$=0.15 (Hex-EtOAc; 9:1); $v_{max}$ (neat/cm$^{-1}$) 2926, 2860, 1738, 1710, 1640, 1461; $\delta_H$ (400 MHz, CDCl$_3$) 0.88 (3H, t, J 6.5 Hz, CH$_3$), 1.21-1.43 (18H, m, CH$_2$), 1.49 (2H, pent, J 7.5 Hz, 5-CH$_2$), 1.65 (2H, pent, J 7.5 Hz, 3-CH$_2$), 1.90 (1H, d, J 7.75 Hz, 7a-CH), 2.13-2.20 (2H, m, 6-CH$_2$), 2.30 (2H, t, J 7.5 Hz, 2-CH$_2$), 2.36 (1H, d, J 7.75 Hz, 3a-CH), 2.57 (1H, d(br), J 7.5 Hz, 1-CH), 2.74 (1H, s(br), 4-CH), 3.04 (1H, s(br), 7-CH), 3.67 (3H, s, CH$_3$), 6.17 (1H, dd, J 3.0, 5.5 Hz, CH), 6.23 (1H, dd, J 3.0, 5.5 Hz, CH), 6.47 (1H, dt, J 2.0, 8.0 Hz, 7-CH); $\delta_C$ (100 MHz, CDCl$_3$) 14.0, 22.59, 24.7, 26.4, 28.3, 28.9, 29.1, 29.2, 29.5, 29.8, 31.8, 33.9, 36.9, 42.9, 43.0, 46.0, 48.0, 49.6, 51.4, 54.4, 137.4, 137.5, 138.8, 145.5, 173.9, 208.2; m/z (CI) 418 (MNH$_4^+$, 5%), 401 (MH$^+$, 10%), 335 (M-C$_5$H$_6^+$, 100%); Found 401.30622, C$_{26}$H$_{41}$O$_3$ requires 401.30557 (+1.8 ppm).

Preparation of (±)-7-[1-octyl-3-oxo-1,3,3a4,7,7a-hexahydro-4,7-methanoinden-(2Z)-ylidene]heptanoic Acid Methyl Ester (6)

Under nitrogen, Et$_2$O (30 cm$^3$) and a 2.0 M solution of octyl magnesium bromide in Et$_2$O (1.33 cm$^3$, 2.66 mmol, 1.5 eq.) was cooled to –78° C. before treatment with CuI (51 mg, 0.27 mmol, 0.1 eq.). This solution was stirred for 1.5 hours, during which time the temperature gradually rose to –25° C. The reaction vessel was re-cooled to –45° C. and the enone (4) (388 mg, 1.78 mmol, 1 eq.) in Et$_2$O (10 cm$^3$) was added. Over 1 hour, the temperature rose to –5° C. TLC analysis (Hex-EtOAc; 9:1) indicated consumption of enone. The temperature was reduced to –78° C. and the aldehyde (3) (422 mg, 2.67 mmol, 1.5 eq.) was added. The reaction was allowed to warm to room temperature over 4 hours. Saturated NH$_4$Cl (50 cm$^3$) was added and the resultant mixture was extracted with Et$_2$O (3×50 cm$^3$. The combined organic extracts were dried over MgSO$_4$, filtered and the solvent removed in vacuo. Purification by flash column chromatography (Hex-EtOAc; 19:1) afforded initially the cis-isomer (6) (266 mg, 37%) as a colourless liquid followed by the trans-isomer (7) (140 mg, 20%). $R_f$=0.2 (Hex-EtOAc; 9:1); $\delta_H$ (400 MHz, CDCl$_3$) 0.89 (3H, t, J 6.5 Hz, CH$_3$), 1.24-1.52 (20H, m, CH$_2$), 1.63 (2H, pent, J 7.5 Hz, 3-CH$_2$), 1.83 (1H, d(br), J 8.0 Hz, 7a-CH), 2.30 (2H, t, J 7.5 Hz, 2-CH$_2$), 2.13-2.20 (2H, m, 6-CH$_2$), 2.29-2.35 (2H, m, 3a-CH, 1-CH), 2.72 (1H, s(br), 4-CH), 3.05 (1H, s(br), 7-CH), 3.66 (3H, s, CH$_3$), 5.85 (1H, dt, J 2.0, 7.5 Hz, 7-CH), 6.17 (1H, dd, J 2.75, 5.5 Hz, CH), 6.21 (1H, dd, J 2.75, 5.5 Hz, CM); $\delta_C$ (100 MHz, CDCl$_3$) 14.1, 22.6, 24.8, 26.4, 27.8, 28.8, 29.0, 29.3, 29.6, 29.8, 31.8, 34.0, 38.7, 43.3, 45.8, 45.85, 47.7, 49.4, 51.4, 55.5, 137.5, 138.6, 141.7, 143.9, 174.1, 209.5; m/z (CI) 418 (MNH$_4^+$, 15%), 401 (MH$^+$, 15%), 335 (M-C$_5$H$_6^+$, 100%); Found 401.30659, C$_{26}$H$_{41}$O$_3$ requires 401.30557 (+2.8 ppm).

Preparation of 7-[2-octyl-5-oxocyclopent-3-en-(E)-ylidene] heptanoic Acid Methyl Ester (8)

Under nitrogen in oven dried glassware, a mixture of 7 (200 mg, 0.50 mmol, 1 eq.) and maleic anhydride (245 mg, 2.50 mmol, 5 eq.) in dichloromethane (20 cm$^3$) was treated with a 1 M solution of MeAlCl$_2$ in hexanes (0.5 cm$^3$, 0.50 mmol, 1 eq.) and heated to 50° C. (oil bath temperature) for 6 hours. The reaction mixture was cooled to room temperature and silica (ca. 2 g) was added. The solvent was removed under reduced pressure and the residue was purified by flash column chromatography (Hex-EtOAc; 4:1) affording the title compound (8) (115 mg, 69%) and its cis-isomer (9) (28 mg, 17%) both as clear liquids. 7-[2-Octyl-5-oxocyclopent-3-en-(E)-ylidene]heptanoic acid methyl ester (8): $R_f$=0.2 (Hex-EtOAc; 3:1); $\delta_H$ (400 MHz, CDCl$_3$) 0.88 (3H, t, J 6.5 Hz, CH$_3$), 1.21-1.34 (12H, m, CH$_2$), 1.34-1.42 (2H, m, CH$_2$), 1.46-1.54 (1H, m, CH$_A$H$_B$), 1.52 (2H, pent, J 7.5 Hz, CH$_2$), 1.65 (2H, pent, J 7.5 Hz, CH$_2$), 1.76-1.86 (1H, m, CH$_A$H$_B$), 2.18-2.32 (2H, m, 6-CH$_2$), 2.31 (2H, t, J 7.5 Hz, 2-CH$_2$), 3.44-3.49 (1H, m, 2-CH), 3.66 (3H, s, CH$_3$), 6.32 (1H, dd, J 2.0, 6.0 Hz, 4-CH), 6.53 (1H, t, J 7.5 Hz, 7-CH), 7.50-7.57 (1H, m, 3-CH); $\delta_C$ (100 MHz, CDCl$_3$) 14.0, 22.6, 24.7, 25.9, 28.3, 28.85, 28.9, 29.2, 29.4, 29.7, 31.8, 32.5, 33.9, 43.3, 51.4, 134.8, 135.1, 138.1, 164.9, 174.0, 196.9; m/z (CI) 352 (MNH$_4^+$, 5%), 335 (MH$^+$, 100%); Found C, 75.33; H, 10.35%, C$_{21}$H$_{34}$O$_3$ requires C, 75.40; H, 10.26%. 7-[2-Octyl-5-oxocyclopent-3-en-(Z)-ylidene]heptanoic acid methyl ester (9): $R_f$=0.25 (Hex-EtOAc; 3:1); $\delta_H$ (400 MHz, CDCl$_3$) 0.88 (3H, t, J 6.5 Hz, CH$_3$), 1.19-1.32 (20H, m, CH$_2$), 2.29 (2H, t, J 7.5 Hz, 2-CH$_2$), 2.80 (2H, q, J 7.5 Hz, 6-CH$_2$), 3.23-3.28 (1H, m, 2-CH), 3.67 (3H, s, CH$_3$), 5.99 (1H, t, J 7.5 Hz, 7-CH), 6.26 (1H, dd, J 2.0, 6.0 Hz, 4-CH), 7.42 (1H, dd, J 2.5, 6.0 Hz, 3-CH); $\delta_C$ (100 MHz, CDCl$_3$) 14.1, 22.6, 24.8, 26.4, 27.0, 28.8, 29.0, 29.2, 29.4, 29.8, 31.8, 33.6, 34.0, 45.5, 51.4, 136.3, 137.1, 139.8, 160.3, 174.1, 198.2; m/z (CI) 352 (MNH$_4^+$, 10%), 335 (MH$^+$, 100%).

EXAMPLE 6

The effect of (–)-$\Delta^{12,14}$-15-deoxy-PG-J$_2$ and compound CTC-150 on the reactivity of transcription factors HSF and NF-κB and on the replication of Sendai virus were tested in the manner described below.

Effect on the Reactivity of Transcription Factors HSF and NF-κB

Human lymphoblastoid Jurkat T cells were grown at 37° C. in a 5% CO$_2$ atmosphere in RPM1 1640 medium (GIBCO BRL, Gaithersburg, Md., United States of America) supplemented with 10% fetal calf serum (FCS, Hyclone Europe Ltd, United Kingdom), 2 mM glutamine and antibiotics according to the method described by A. Rossi et al.[48] The test compound was stored as a 100% ethanolic stock solution (100 mM) or in dimethylsulfoxide (100 mM) and diluted to the appropriate concentration in culture medium at the time of use. Cells were treated with different concentrations of test compound for 1 hour and then stimulated with 12-O-tetradecanoylphorbol-13-acetate (TPA, 25 ng/ml), which is a strong inducer of NF-κB. Control cells received an equal amount of control diluent. After 3 hours, whole-cell extracts were prepared and subjected to analysis of DNA-binding activity by EMSA (Electrophoretic Mobility Shift Assay) for detection of HSF or NF-κB activation, according to the method described by A. Rossi et al.[48]

Specificity of protein-DNA complexes was verified by immunoreactivity with polyclonal antibodies specific for p65 (Rel A) or for HSF-1, for NF-κB and HSF respectively. Quantitative evaluation of NF-κB- and HSF-DNA complex formation was determined by Molecular Dynamics PhosphorImager (MDP) analysis and was expressed in arbitrary units, as described by A. Rossi et al.[49] The results for (–)-$\Delta^{12,14}$-15-deoxy-PG-J$_2$ are shown in FIG. 1. These results show the latter compound to be a potent inhibitor of NF-κB.

By way of comparison, the concentration of compound CTC-150 required to give an HSF activation to 200% of its original level was found to be 0.02 µM, whilst the concentration of compound CTC-150 required to give an NF-κB inhibition to 50% of its original level was found to be $IC_{50}=7$ µM. These results show compound CTC-150 is also a potent inhibitor of NF-κB.

Effect on the Replication of Sendai Virus

Figure 2:
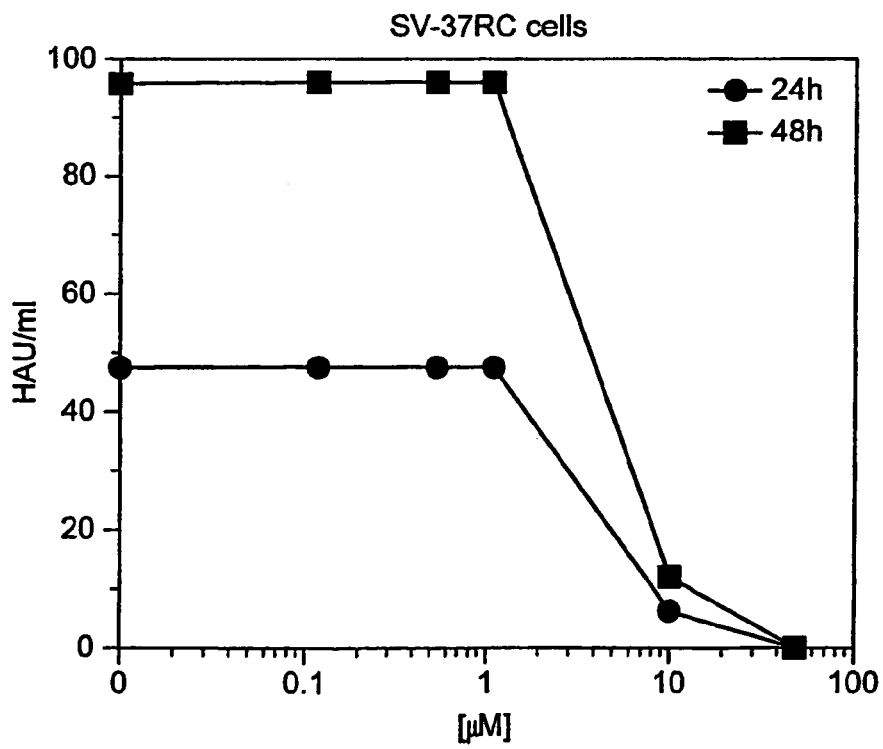
FIG. 2 shows the results of a test, described in Example 6, of the effect of (-)-$\Delta^{12,14}$-15-deoxy-PG-$J_2$ on the Sendai virus replication.

Monkey kidney 37RC cells were grown at 37° C. under the conditions described above for human lymphoblastoid Jurkat T cells. The parainfluenza Sendai virus (SV) was grown in the allantoic cavity of 10 day-old embryonated eggs. Viral titre was expressed in haemagglutinating units (HAU) per ml; haemagglutinin titration was carried out according to standard procedures using human 0 Rh+ erythrocytes, as described in C. Amici et al.[50] Confluent monolayers of 37RC cells were infected with SV virus (5 HAU/$10^5$ cells) for 1 hour at 37° C., and then treated with different concentrations of test compound. Virus yield at 24 hours after infection was determined in the supernatant of infected cells by HAU titration. The results for $(-)-\Delta^{12,14}$-15-deoxy-PG-$J_2$ are shown in FIG. 2. These results show the latter to be a potent inhibitor of Sendai virus replication.

The $ID_{50}$ (the 50% inhibitory dose/concentration) value at 24 hours and the $TD_{100}$ (the dose or concentration at which a tested compound is 100% toxic to uninfected cells, determined visually by microscopy) for both $(-)-\Delta^{12,14}$-15-deoxy-PG-$J_2$ and for compound CTC-150 were measured and the following results were obtained.

| Compound | ID50/µM | TD100/µM |
|---|---|---|
| $(-)-\Delta^{12,14}$-15-deoxy-PG-$J_2$ | 3.0 | 50 |
| CTC-150 | 0.7 | >50 |

These results show that the antiviral effect of both compounds takes place at a concentration at which they are non-toxic to 37RC cells, and also that compound CTC-150 was over 4 times more active than $(-)-\Delta^{12,14}$-15-deoxy-PG-$J_2$.

REFERENCES

1. U.S. von Euler, *Arch. Exp. Pathol. Pharmakol*, 1934, 175, 78.
2. Early, chemistry-based studies are described in J. S. Bindra and R, Bindra, "Prostaglandin Synthesis", Academic Press, New York, 1977; A. Mitra, "The Synthesis of Prostaglandins" Wiley, New York, 1977.
3. For example, the albumin-catalysed metabolism of PG-$D_2$ has been studied, F. A. Fitzpatrick and M. A. Wynalda, *J. Biol. Chem.*, 1983, 258, 11713.
4. B. Ashly in "Human Pharmacology—Molecular to Clinical" 3rd edn. (eds. T. M. Brody, J. Larner, K. P. Minneman and H. C. Neu), Mosby, 1994, 225.
5. T. Kato, M. Fukushima, S. Kurozumi and R. Noyori, *Cancer Res.*, 1986, 46, 3538; M. Fukushima, T. Kato, S. Narumiya, Y. Mizushima, H. Sasaki, Y. Terashima, Y. Nishiyama and M. G. Santoro, *Adv. Prostaglandin, Thromboxane and Leukotriene Res.*, 1989, 19, 415.
6. M. Tanikawa, K Yamada, K. Tominaga, H. Morisaki, Y. Kaneko, K. Ikeda, M. Suzuki, T. Kiho, K. Tomokiyo, K. Furuta, R. Noyori and M. Nakanishi, *J. Biol Chem.*, 1998, 273, 18522; M. G. Santoro, E. Garaci and C. Amici, *Proc. Nat. Acad. Sci.*, 1989, 86, 8407.
7. H. Sasaki and M. Fukushima, *Anti-Cancer Drugs*, 1994, 5, 131.
8. I. Vedin, J. Wasserman and S. Hammarstrom, *Prostaglandins, Leukotrienes, Essential Fatty Acids*, 1996, 55, 185.
9. K. Suzuki, F. Shono and M. Uyeda, *Biosci. Biotechnol. Biochem.*, 1998, 62, 2073.
10. Y. Kawamoto, Y. Nakamura, Y. Naito, Y. Torii, T. Kumagai, T. Osawa, H. Ohigashi, K Satoh, M. Imagawa and K. Uchida, *J. Biol. Chem.*, 2000, 275, 11291.
11. C. Amici, A. T. Palamara, E. Garaci and M. G. Santoro, *Antiviral Res.* 1992, 19, 129; F. Pica, F. Decesare and M. G. Santoro, ibid, 1993, 20, 193; M. G. Santoro, *Trends in Microbiol.*, 1997, 5, 276.
12. C. Amici and M. G. Santoro, unpublished results.
13. G. Conti, P. Pottincasa, S. Visalli and C. Chezzi, *Virus Res.*, 2001, 75, 43.
14. C. Conti, P. Mastromarino, P. Tomao, A. De Marco, F. Pica and M. G. Santoro, *Antimicrobial Agents Chemother.*, 1996, 40, 367.
15. C. Rozero, A. Carattoli, A. De Marco, C. Amici, C. Giorgi and M. G. Santoro, *J. Chem. Invert.*, 1996, 97, 1795.
16. G. Elia, B. Polla, A. Rossi and M. G. Santoro, *Eur. J. Biochem.*, 1999, 264, 736; cells may also be protected against the deleterious effects of oxidized low-density lipoproteins, L. Hamel, M. Kenney, K. Clark, L. Merkel and C. Rojas, *Biochem. Biophys. Res. Commun.*, 2000, 269, 327.
17. F. Pica, A. T. Palamara, A. Rossi, A. De Marco, C. Amici and M. G. Santoro, *Antimicrobial Agents Chemother.*, 2000, 44, 200.
18. A. Rossi, P. Kapati, G. Natoli, T. Takahasi, Y. Chen, M. Karin and M. G. Santoro, *Nature*, 2000, 403, 103; D. S. Straus, G. Pascual, M. Li, J. S. Welch, M. Ricote, C. H. Hsiang, L. L. Sengchanthalangsy, G. Ghosh and C. K. Glass, *Proc. Natl. Acad. Sci. USA*, 2000, 97, 4844; A. Castrillo, M. J. M. Diaz-Guerra, S. Hortelano, P. Martin-Sanz and L. Bosca, *Mol. Cellular Biol.*, 2000, 20, 1692; see also T. Koizumi, M. Negishi and A. Ichikawa, *Biochem. Pharmacol.*, 1993, 45, 2457.
19. M. Sazuki, M. Mori, T. Niwa, R. Hirata, K. Furuta, T. Ishikawa and R. Noyori, *J. Am. Chem. Soc.*, 1997, 119, 2376.
20. T. Koizumi, M. Negishi and A. Ichikawa, *Biochem. Pharmacol*, 1993, 45, 2457; J. J. P. Bogards, J. C. Venekamp and P. J. van Bladeren, *Chem. Res. Toxicol*, 1999, 10, 310; M. L. P. S. van Iersel, P. J. van Bladeren, N. H. P. Cnubben, J. H. Koeman and N. Smink, *Biochem. Pharmacol.*, 1999, 57, 1383.
21. M. Kondo, T. Oya-Ito, T. Kumagi, T. Osawa and K. Uchida, *J. Bios Chem.* 2001, 276, 12076.
22. B. M. Forman, P. Tontonoz, J. Chen, R. P. Brun, B. M. Spiegelman and R. M. Evans, *Cell*, 1995, 83, 803; S. A. Kliewer, J. M. Lenhard, T. M. Willson, I. Patel, D. C. Morris and J. M. Lehmann, ibid, 1995, 83, 813.
23. K. Guyton, R. Bond, C. Reilly, G. Gilkeson, P. Halushka and J. Cook, *J. Leukocyte Biol,.* 2001, 69, 631.
24. M. Rocte, A. C. Li, T. M. Willson, C. J. Kelly and C. K. Glass, *Nature*, 1998, 391, 79; D. A. Willoughby, A. R. Moore and P. R. Colville-Nash, *Nature Med.*, 2000, 6, 137; P. R. Colville-Nash, S. S. Qureshi, D. Willis and D. A. Willoughby, *J. Immunol,.* 1998, 161, 987; Y. Kitomura, J. Kakimura, Y. Matsuoka, Y. Nomura, P. J. Gebicke-Haerter and T. Taniguchi; *Neurosci. Lett,.* 1999, 262, 129; T. V. Petrova, K. T. Akoma and L. J. Van Eldik, *Proc. Natl. Acad. Sci.* USA,. 1999, 96, 4668.
25. A. Chawla, Y. Barak, L. Nagy, D. Liao, P. Tontonez and R. M. Evans, *Nature Med* 2001, 7, 48.

26. Y. Tsubouchi, Y. Kawahito, M. Kohno, K. Inoue, T. Hla and H. Sano, *Biochem. Biophys. Res. Commun,*. 2001, 283, 750.
27. B. Poligone and A. S. Baldwin, *J. Biol. Chem,.* 2001, 276, 38658.
28. C. Amici, G. Belardo, A. Rossi and M. G. Santoro, *J. Biol. Chem,.* 2001, 276, 28759.
29. B. H. Rovin, L. Lu and A. Cosio, *J. Am. Soc. Nephrol,.* 2001, 12, 1659; E. Cernuda-Morollon, E. Pineda-Molina, F. J. Canada and D. Perez-Sala, *J. Biol. Chem,.* 2001, 276, 35530; S. G. Harris and R. P. Phipps, *Eur. J. Immunol,.* 2001, 31, 1098.
30. X. H. Xin, S. Y. Yang, J. Kowalski and M. E. Gerritsen, *J. Biol. Chem,.* 1999, 274, 9116; D. Bishop-Bailey and T. Hta, ibid, 1999, 274, 17042.
31. G. Fibl, M. N. Wente, H. A. Reber and O. J. Hines, *Biochem. Biophys. Res. Commun,.* 2001, 287, 522.
32. Y. Tsubouchi, H. Sano, Y. Kawahito, S. Mukai, R. Yamada, M. Kohno, K Inoue, T. Hla and M. Kondo, *Biochem. Biophys. Res. Commun,.* 2000, 270, 400.
33. J. E. Mullally, P. J. Moos, K. Edes and F. A. Fitzpatrick, *J. Biol. Chem,.* 2001, 276, 30366.
34. R. Butler, S. H. Mitchell, D. J. Tindell and C. Y. F. Young, *Cell Growth and Differentiation*, 2000, 11, 49.
35. R. N. DuBois, R. Gupta, J. Brockman, B. S. Reddy, S. L. Krakow and M. A. Lazar, *Carcinogenesis*, 1998, 19, 49; K. Ohta, T. Endo, K. Haraguchi, J. M. Hershman and T. Onaya, *J. Clin. Endocrinol. Metab,.* 2001, 86, 2170.
36. R. Chinery, R. J. Coffey, R. Graves-Deal, S. C. Kirkland, S. C. Sanchez, W. E. Zackert, J. A. Oates and J. D. Morrow, *Cancer Res,.* 1999, 59, 2739.
37. R. Noyori and M. Suzuki, *Angew. Chem. Int. Ed*. 1984, 23, 847.
38. R. Noyori, H. Koyano, M. Mori, R Hirata, Y. Shiga, T. Kokura and M. Suzuki, *Pure and Appl. Chem,.* 1994, 66, 1999.
39. M. Suzuki, T. Kawagishi, A. Yanagisawa, T. Suzuki, N. Okamura and R. Noyori, *Bull. Chem. Soc,.* 1988, 61, 1299.
40. S. Fukushima, Y. Takeuchi, S. Kishimoto, S. Yamashita, K Uetsuki, S. Shirakawa, M. Suzuki, K. Furuta, R. Noyori, H. Sasaki Y. Kikuchi, T. Kita, T. Yamori, J. Sawada, M. Kojima, A. Hazato, S. Kurozumi and M. Fukushima, *Anti-Cancer Drugs*, 2001, 12, 221.
41. O. Tsuge, S. Kinemasa and Y. Ninomiya, *Chem. Lett,.* 1984, 1993.
42. J. Tanaka, S. Kanemasa, Y. Ninomiya and O. Tsuge, *Bull. Chem. Soc. Jpn,.* 1990, 63, 466.
43. J. Tanaka, H. Kobayashi, S. Kanemasa and O. Tsuge, *Bull. Chem. Soc. Jpn,.* 1989, 62, 1193.
44. A. R. Bassindale, I. Katampe, P. A. Kyle and P. G. Taylor, *J. Chem. Soc., Perkin Trans. I*, 1996, 327.
45. T. Ito, S. Okanoto and F. Sato, *Tetrahedron Lett,.* 1990, 31, 6399.
46. U. Khand et al., *J. Chem. Soc., Perkin Trans. I,* 1973, 977.
47. X. Verdaguer et al., *J. Am. Chem. Soc,.* 2000, 122, 10242.
48. A. Rossi et al., *Proc. Natl. Acad. Sc.* USA, 1997, 94: 746-750.
49. A. Rossi et al., *J. Biol. Chem.* 1998, 273: 16446-16452.
50. C. Amici et al., *J. Virol*, 1994, 68: 6890-6899.

The invention claimed is:

1. A method for preparing a compound of the formula (I)

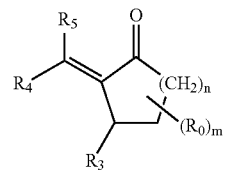

wherein $R_0$ is hydrogen or any other substituent;
$R_3$, $R_4$ and $R_5$ are each, independently, hydrogen or a substituted or unsubstituted alkyl, alkenyl, alkynyl, cycloalkyl, cycloalkenyl, cycloalkynyl, aryl or aralkyl group, optionally including at least one heteroatom in its carbon skeleton, or $R_3$ and $R_4$ together form part of a single or fused ring structure, optionally including at least one heteroatom in its carbon skeleton;

n=0 to 100; and m=0 to (n×1), which comprises reacting a compound of the formula (II)

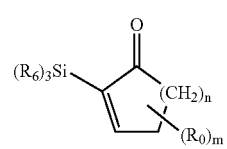

wherein $R_6$ is a substituted or unsubstituted alkyl, alkenyl, alkynyl, cycloalkyl, cycloalkenyl, cycloalkynyl, aryl or aralkyl group, optionally including at least one heteroatom in its carbon skeleton, each $R_6$ group being the same or different,
with an organometallic compound of the formula (III)

 (III)

wherein M is a metal ion of an organometallic complex,
and reacting the conjugate addition product so obtained in situ with a compound of the formula (IV)

to form a compound of the formula (I).

2. A method as in claim 1, for preparing a compound of the formula (V),

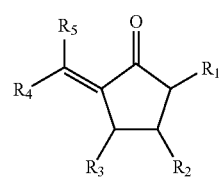

wherein $R_1$ and $R_2$ are each, independently, hydrogen, hydroxyl, cyano or a halogen group, or a substituted or unsubstituted alkyl, alkenyl, alkynyl, cycloalkyl, cycloalkenyl, cycloalkynyl, aryl, or aralkyl group, optionally including at least one heteroatom in its carbon skeleton, or $R_1$ and $R_2$ together form part of a single or fused ring structure, optionally including at least one heteroatom in its carbon skeleton, which comprises reacting a compound of the formula (VI)

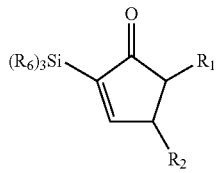

(VI)

with an organometallic compound of the formula (III)

$R_3M$ (III)

and reacting the conjugate addition product so obtained in situ with a compound of the formula (IV)

$R_4COR_5$ (IV)

to form a compound of the formula (V).

3. A method as in claim 2, wherein the compound of the formula (VI) is reacted with the compound of the formula (III) so that conjugate addition occurs diastereoselectively.

4. A method as in claim 3, wherein the compound of the formula (VI) or the compound of the formula (III) is chiral.

5. A method as in claim 3, wherein at least one $R_6$ group is a chiral auxiliary.

6. A method as in claim 1 or 2, wherein at least one $R_6$ group forms a linker group that links the compound of the formula II or VI to a solid phase.

7. A method as in claim 1 or 2, wherein the organometallic compound of the formula (III) is an organozinc, organocadmium, organolithium or an organomagnesium complex.

8. A method as in claim 7, wherein the organometallic complex is a copper lithium complex of the formula (VIII)

$R_3R_7CuLi$ (VIII)

wherein $R_7$ is, independently, hydrogen or a substituted or unsubstituted alkyl, alkenyl, alkynyl, cycloalkyl, cycloalkenyl, cycloalkynyl, aryl or aralkyl group, optionally including at least one heteroatom in its carbon skeleton.

9. A method as in claim 8, wherein $R_3$ and $R_7$ are the same.

10. A method as in claim 7, wherein the organometallic complex is a Grignard reagent of the formula (IX)

$R_3MgX$ (IX)

wherein $R_3$ is hydrogen or a substituted or unsubstituted alkyl, alkenyl, alkynyl, cycloalkyl, cycloalkenyl, cycloalkynyl, aryl or aralkyl group, optionally including at least one heteroatom in its carbon skeleton, and X is a halogen group.

11. A method as in claim 10, wherein the Grignard reagent of the formula (IX) is used in conjunction with a catalyst that promotes conjugate addition, such as copper (I) iodide.

12. A method as in claim 1 or 2, wherein each of $R_3$ and $R_4$ is a substituted or unsubstituted alkyl, alkenyl or alkynyl group having from 1 to 12 carbon atoms, optionally including at least one heteroatom in its carbon skeleton, and $R_5$ is hydrogen or an alkyl group having from 1 to 3 carbon atoms, optionally including at least one heteroatom in its carbon skeleton.

13. A method as in claim 2, which further comprises the step of reacting a compound of the formula (X)

with a trisubstituted-silanylacetylene and $Co_2(CO)_8$, to form the compound of the formula (VI).

14. A method as in claim 13, wherein at least one $R_6$ group is a chiral auxiliary and the compound of formula (VI) is formed diastereoselectively.

15. A method as in claim 14, wherein said at least one $R_6$ group is α-pinene.

16. A method for preparing a compound of the formula (XI)

wherein $R_4$ and $R_3$ are each, independently, hydrogen or a substituted or unsubstituted alkyl, alkenyl, alkynyl, cycloalkyl, cycloalkenyl, cycloalkynyl, aryl or aralkyl group, optionally including at least one heteroatom in its carbon skeleton, or $R_3$ and $R_4$ together form part of a single or fused ring structure, optionally including at least one heteroatom in its carbon skeleton, which comprises preparing a compound of the formula (V) by a method as in claim 2 and treating the compound of the formula (V) so that it undergoes simultaneous elimination of $R_1$ and $R_2$, to form the compound of the formula (XI).

17. A method as in claim 16, wherein one of $R_1$ and $R_2$ is hydrogen and the other is hydroxyl and the compound of the formula (V) undergoes dehydration, to form the compound of the formula (XI).

18. A method as in claim 16, wherein one of $R_1$ and $R_2$ is hydrogen and the other is a halogen group and the compound of the formula (V) undergoes dehydrohalogenation, to form the compound of the formula (XI).

19. A method as in claim 16, wherein the compound of the formula (V) is a compound of the formula (XII)

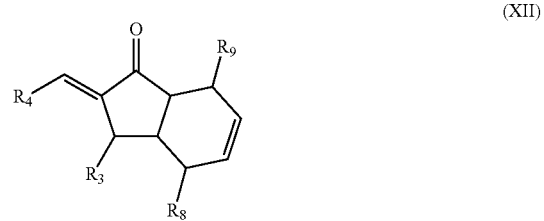

wherein $R_8$ and $R_9$ are each, independently, hydrogen or a substituted or unsubstituted alkyl, alkenyl, alkynyl, cycloalkyl, cycloalkenyl, cycloalkynyl, aryl, or aralkyl group, optionally including at least one heteroatom in its carbon skeleton, or $R_8$ and $R_9$ together form part of a single or a fused ring structure, optionally including at least one heteroatom in its carbon skeleton, and wherein the compound of the formula (XII) undergoes a Retro Diels-Alder reaction to form the compound of the formula (XI).

20. A method as in claim 19, wherein $R_8$ and $R_9$ together form a —$CH_2$— or —$CH_2CH_2$— group.

21. A method for preparing a compound of the formula (XIII)

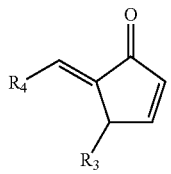
(XIII)

wherein $R_3$ and $R_4$ are each, independently, a substituted or unsubstituted alkyl, alkenyl, alkynyl, cycloalkyl, cycloalkenyl, cycloalkynyl, aryl or aralkyl group, optionally including at least one heteroatom in its carbon skeleton, or $R_3$ and $R_4$ together form part of a single or a fused ring structure, optionally including at least one heteroatom in its carbon skeleton;

which comprises reacting norbornadiene with trimethylsilanylacetylene and $CO_2(CO)_8$ to form a compound of the formula (XIV)

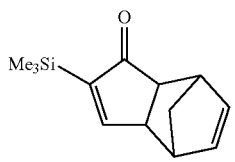
(XIV)

reacting the compound of the formula (XIV) with an organometallic compound of the formula (III)

$R_3M$ (III)

wherein M is a metal ion of an organometallic complex, and reacting the resultant conjugate addition product in situ with a compound of the formula (XV)

$R_4CHO$ (XV)

to form a compound of the formula (XVI)

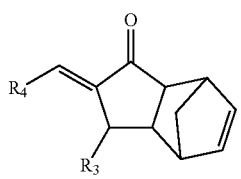
(XVI)

and heating the compound of the formula (XVI) to form the compound of the formula (XIII).

22. A method as in claim 21, for preparing a compound of the formula (XVII)

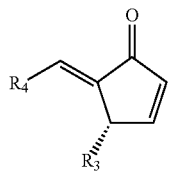
(XVII)

wherein $R_3$ and $R_4$ are each, independently, a substituted or unsubstituted alkyl, alkenyl, alkynyl, cycloalkyl, cycloalkenyl, cycloalkynyl, aryl or aralkyl group, optionally including at least one heteroatom in its carbon skeleton, or $R_3$ and $R_4$ together form part of a single or a fused ring structure, optionally including at least one heteroatom in its carbon skeleton;

which comprises reacting norbornadiene with trimethylsilanylacetylene and $Co_2(CO)_8$ asymmetrically to form a compound of the formula (XVIII)

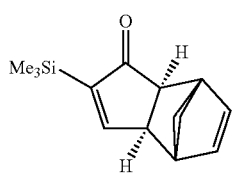
(XVIII)

reacting the compound of the formula (XVIII) with an organometallic compound of the formula (III)

$R_3M$ (III)

wherein M is a metal ion of an organometallic complex, and reacting the resultant conjugate addition product in situ with a compound of the formula (XV)

$R_4CHO$ (XV)

to form a compound of the formula (XIX)

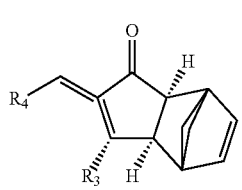
(XIX)

and heating the compound of the formula (XIX) to form the compound of the formula (XVII).

23. A method as in claim 21, for preparing a compound of the formula (XX)

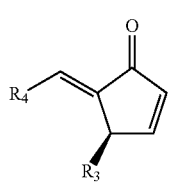
(XX)

wherein $R_3$ and $R_4$ are each, independently, a substituted or unsubstituted alkyl, alkenyl, alkynyl, cycloalkyl, cycloalkenyl, cycloalkynyl, aryl or aralkyl group, optionally including at least one heteroatom in its carbon skeleton, or $_3$ and $R_4$ together form part of a single or a fused ring structure, optionally including at least one heteroatom in its carbon skeleton;

which comprises reacting norbornadiene with trimethylsilanylacetylene and $Co_2(CO)_8$ asymmetrically to form a compound of the formula (XXI)

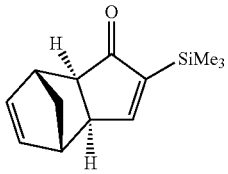
(XXI)

reacting the compound of the formula (XXI) with an organometallic compound of the formula (III)

$R_3M$ (III)

wherein M is a metal ion of an organometallic complex, and reacting the resultant conjugate addition product in situ with a compound of the formula (XV)

$R_4CHO$ (XV)

to form a compound of the formula (XXII)

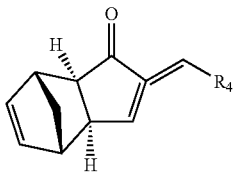
(XXII)

and heating the compound of the formula (XXII) to form the compound of the formula (XX).

24. A method as in claim 21, 22 or 23, wherein the organometallic compound of the formula (III) is a copper lithium complex of the formula (VIII)

$R_3R_7CuLi$ (VIII).

25. A method as in one of claims 21 to 23, wherein the compound of the formula (XVI), (XIX) or (XXII) is heated in the presence of a Lewis acid.

26. A method as in claim 25, wherein the Lewis acid is $MeAlCl_2$ or $Me_2AlCl$.

27. A method as in one of claims 21 to 23, wherein the compound of the formula (XVI), (XIX) or (XXII) is heated in the presence of a dienophile.

28. A method as in claim 27, wherein the dienophile is maleic anhydride.

29. A compound having the following structure:

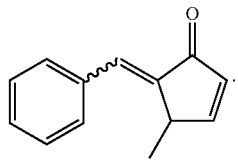

30. A compound having the following structure:

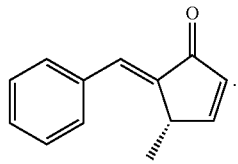

31. A pharmaceutical composition comprising a compound as in claim 29 or 30 and a pharmaceutically acceptable excipient.

32. A method of treating a patient in need of anti-viral therapy, cancer therapy or anti-inflammatory therapy, comprising administering a therapeutically effective amount of a compound as in claim 29 or 30 to said patient.

33. A method as in claim 4, wherein at least one $R_6$ group is a chiral auxiliary.

34. A method as in claim 2, 3, 4, 5 or 33, wherein the compound of the formula (VI) and the compound of the formula (III) form an enolate of the formula (VII).

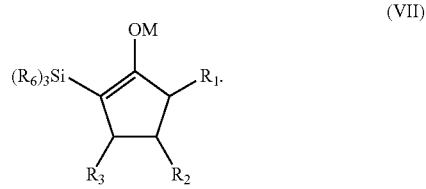
(VII)

* * * * *